(12) United States Patent
O'Malley et al.

(10) Patent No.: US 11,439,418 B2
(45) Date of Patent: Sep. 13, 2022

(54) CLOT RETRIEVAL DEVICE FOR REMOVING CLOT FROM A BLOOD VESSEL

(71) Applicant: Neuravi Limited, Galway (IE)

(72) Inventors: Thomas O'Malley, Galway (IE); Aidan Duffy, Galway (IE); Declan Lee, Galway (IE); AnnaLisa Smullin, Galway (IE); Gillian Gunning, Galway (IE); Diarmaid O'Keeffe, Galway (IE)

(73) Assignee: Neuravi Limited, Galway (IE)

( * ) Notice: Subject to any disclaimer, the term of this patent is extended or adjusted under 35 U.S.C. 154(b) by 0 days.

(21) Appl. No.: 16/946,467

(22) Filed: Jun. 23, 2020

(65) Prior Publication Data
US 2021/0393279 A1 Dec. 23, 2021

(51) Int. Cl.
*A61B 17/221* (2006.01)
*A61B 90/00* (2016.01)

(52) U.S. Cl.
CPC ............ *A61B 17/221* (2013.01); *A61B 90/39* (2016.02); *A61B 2017/2215* (2013.01); *A61B 2090/3966* (2016.02)

(58) Field of Classification Search
CPC .......... A61B 17/221; A61B 2017/2215; A61B 2017/2212; A61B 17/22031; A61B 2017/22035; A61B 2017/22034; A61B 17/320725; A61B 2017/320716;
(Continued)

(56) References Cited

U.S. PATENT DOCUMENTS

| 2,828,147 A | 3/1958 | Peiffer |
| 3,361,460 A | 1/1968 | Gerhart |
| 4,455,717 A | 6/1984 | Gray |

(Continued)

FOREIGN PATENT DOCUMENTS

| CN | 2557083 Y | 6/2003 |
| CN | 101172051 A | 5/2008 |

(Continued)

OTHER PUBLICATIONS

US 6,348,062 B1, 02/2002, Hopkins (withdrawn)
(Continued)

*Primary Examiner* — Wade Miles
(74) *Attorney, Agent, or Firm* — Troutman Pepper Hamilton Sanders LLP

(57) ABSTRACT

A clot retrieval device is disclosed to remove clot from a blood vessel. The device can include a collapsed configuration and an expanded configuration. The device can include an inner expandable body with a framework of struts. The device can include an outer expandable body with a framework of struts that at least partially radially surrounding the inner expandable body. A distal portion of the outer expandable body can extend in the deployed configuration towards the outer expandable body to a greater extent than the inner expandable body, closed cells of the distal portion distally tapering and being smaller than cells proximal thereof in the outer expandable body. The plurality of closed cells of the distal portion can include a pair of axially aligned smaller diamond shaped cells formed by struts of the distal portion and positioned along upper and lower regions of the distal portion.

18 Claims, 12 Drawing Sheets

(58) Field of Classification Search
CPC .......... A61F 2/012; A61F 2/013; A61F 2/014; A61F 2/015; A61F 2002/9528; A61F 2002/9534
See application file for complete search history.

(56) References Cited

U.S. PATENT DOCUMENTS

| | | |
|---|---|---|
| 4,611,594 A | 9/1986 | Grayhack et al. |
| 4,612,931 A | 9/1986 | Dormia |
| 4,793,348 A | 12/1988 | Palmaz |
| 4,873,978 A | 10/1989 | Ginsburg |
| 5,011,488 A | 4/1991 | Ginsburg |
| 5,084,065 A | 1/1992 | Weldon et al. |
| 5,092,839 A | 3/1992 | Kipperman |
| 5,100,423 A | 3/1992 | Fearnot |
| 5,102,415 A | 4/1992 | Guenther et al. |
| 5,108,419 A | 4/1992 | Reger et al. |
| 5,122,136 A | 6/1992 | Guglielmi et al. |
| 5,163,951 A | 11/1992 | Pinchuk et al. |
| 5,171,233 A | 12/1992 | Amplatz |
| 5,171,259 A | 12/1992 | Inoue |
| 5,217,441 A | 6/1993 | Shichman |
| 5,234,437 A | 8/1993 | Sepetka |
| 5,236,447 A | 8/1993 | Kubo et al. |
| 5,330,482 A | 7/1994 | Gibbs |
| 5,383,887 A | 1/1995 | Nadal |
| 5,387,219 A | 2/1995 | Rappe |
| 5,387,226 A | 2/1995 | Miraki |
| 5,449,372 A | 9/1995 | Schmaltz |
| 5,499,985 A | 3/1996 | Hein et al. |
| 5,538,512 A | 7/1996 | Zenzon et al. |
| 5,538,515 A | 7/1996 | Kafry et al. |
| 5,549,626 A | 8/1996 | Miller et al. |
| 5,558,652 A | 9/1996 | Henke |
| 5,609,627 A | 3/1997 | Goicoechea |
| 5,624,461 A | 4/1997 | Mariant |
| 5,639,277 A | 6/1997 | Mariant |
| 5,639,278 A | 6/1997 | Dereume et al. |
| 5,645,558 A | 7/1997 | Horton |
| 5,653,605 A | 8/1997 | Woehl et al. |
| 5,658,296 A | 8/1997 | Bates |
| 5,665,117 A | 9/1997 | Rhodes |
| 5,695,519 A | 12/1997 | Summer et al. |
| 5,709,704 A | 1/1998 | Nott et al. |
| 5,713,853 A | 2/1998 | Clark |
| 5,769,871 A | 6/1998 | Mers Kelly |
| 5,769,884 A | 6/1998 | Solovay |
| 5,779,686 A | 7/1998 | Sato et al. |
| 5,779,716 A | 7/1998 | Cano |
| 5,800,519 A | 9/1998 | Sandock |
| 5,810,874 A | 9/1998 | Lefebvre |
| 5,814,064 A | 9/1998 | Daniel |
| 5,827,304 A | 10/1998 | Hart |
| 5,853,422 A | 12/1998 | Huebsch et al. |
| 5,855,598 A | 1/1999 | Pinchuk |
| 5,893,869 A | 4/1999 | Barnhart et al. |
| 5,895,398 A | 4/1999 | Wensel |
| 5,897,567 A | 4/1999 | Ressemann |
| 5,904,698 A | 5/1999 | Thomas et al. |
| 5,911,702 A | 6/1999 | Romley |
| 5,911,725 A | 6/1999 | Boury |
| 5,919,126 A | 7/1999 | Armini |
| 5,931,509 A | 8/1999 | Bartholomew |
| 5,935,139 A | 8/1999 | Bates |
| 5,947,995 A | 9/1999 | Samuels |
| 6,063,113 A | 5/2000 | Kavteladze |
| 6,066,149 A | 5/2000 | Samson et al. |
| 6,066,158 A | 5/2000 | Engelson |
| 6,093,196 A | 7/2000 | Okada |
| 6,093,199 A | 7/2000 | Brown et al. |
| 6,096,053 A | 8/2000 | Bates |
| 6,099,534 A | 8/2000 | Bates |
| 6,099,559 A | 8/2000 | Nolting |
| 6,102,932 A | 8/2000 | Kurz |
| 6,106,548 A | 8/2000 | Roubin |
| 6,129,739 A | 10/2000 | Khosravi |
| 6,143,022 A | 11/2000 | Shull et al. |
| 6,146,404 A | 11/2000 | Kim |
| 6,156,064 A | 12/2000 | Chouinard |
| 6,165,194 A | 12/2000 | Denardo |
| 6,165,199 A | 12/2000 | Barbut |
| 6,168,604 B1 | 1/2001 | Cano |
| 6,168,622 B1 | 1/2001 | Mazzocchi |
| 6,174,318 B1 | 1/2001 | Bates et al. |
| 6,179,861 B1 | 1/2001 | Khosravi |
| 6,203,561 B1 | 3/2001 | Ramee |
| 6,214,026 B1 | 4/2001 | Lepak |
| 6,221,006 B1 | 4/2001 | Dubrul |
| 6,231,597 B1 | 5/2001 | Deem et al. |
| 6,238,412 B1 | 5/2001 | Dubrul |
| 6,245,012 B1 | 6/2001 | Kleshinski |
| 6,245,087 B1 | 6/2001 | Addis |
| 6,251,122 B1 | 6/2001 | Tsukernik |
| 6,254,571 B1 | 7/2001 | Hart |
| 6,264,663 B1 | 7/2001 | Cano |
| 6,267,777 B1 | 7/2001 | Bosma et al. |
| 6,290,710 B1 | 9/2001 | Cryer et al. |
| 6,312,444 B1 | 11/2001 | Barbut |
| 6,315,778 B1 | 11/2001 | Gambale |
| 6,325,815 B1 | 12/2001 | Kusleika |
| 6,325,819 B1 | 12/2001 | Pavcnik |
| 6,334,864 B1 | 1/2002 | Amplatz |
| 6,336,934 B1 | 1/2002 | Gilson et al. |
| 6,346,116 B1 | 2/2002 | Brooks |
| 6,348,056 B1 | 2/2002 | Bates |
| 6,350,271 B1 | 2/2002 | Kurz et al. |
| 6,355,057 B1 | 3/2002 | DeMarais et al. |
| 6,361,545 B1 | 3/2002 | Macoviak |
| 6,364,895 B1 | 4/2002 | Greenhalgh |
| 6,375,668 B1 | 4/2002 | Gifford |
| 6,375,670 B1 | 4/2002 | Greenhalgh |
| 6,383,205 B1 | 5/2002 | Samson et al. |
| 6,383,206 B1 | 5/2002 | Gillick |
| 6,391,037 B1 | 5/2002 | Greenhalgh |
| 6,402,771 B1 | 6/2002 | Palmer |
| 6,416,541 B2 | 7/2002 | Denardo |
| 6,425,909 B1 | 7/2002 | Dieck et al. |
| 6,428,558 B1 | 8/2002 | Jones |
| 6,432,122 B1 | 8/2002 | Gilson et al. |
| 6,436,112 B2 | 8/2002 | Wensel |
| 6,458,139 B1 | 10/2002 | Palmer |
| 6,485,497 B2 | 11/2002 | Wensel |
| 6,485,501 B1 | 11/2002 | Green |
| 6,485,502 B2 | 11/2002 | Don Michael |
| 6,488,701 B1 | 12/2002 | Nolting et al. |
| 6,511,492 B1 | 1/2003 | Rosenbluth |
| 6,530,935 B2 | 3/2003 | Wensel |
| 6,530,939 B1 | 3/2003 | Hopkins |
| 6,540,768 B1 | 4/2003 | Diaz et al. |
| 6,544,279 B1 | 4/2003 | Hopkins |
| 6,551,341 B2 | 4/2003 | Boylan et al. |
| 6,551,342 B1 | 4/2003 | Shen et al. |
| 6,575,996 B1 | 6/2003 | Denison |
| 6,575,997 B1 | 6/2003 | Palmer et al. |
| 6,582,448 B1 | 6/2003 | Boyle |
| 6,585,756 B1 | 7/2003 | Strecker |
| 6,589,265 B1 | 7/2003 | Palmer et al. |
| 6,592,607 B1 | 7/2003 | Palmer et al. |
| 6,592,614 B2 | 7/2003 | Lenker et al. |
| 6,592,616 B1 | 7/2003 | Stack |
| 6,598,265 B2 | 7/2003 | Lee |
| 6,602,265 B2 | 8/2003 | Dubrul |
| 6,602,271 B2 | 8/2003 | Adams |
| 6,602,272 B2 | 8/2003 | Boylan et al. |
| 6,605,102 B1 | 8/2003 | Mazzocchi |
| 6,610,077 B1 | 8/2003 | Hancock et al. |
| 6,616,679 B1 | 9/2003 | Khosravi |
| 6,632,241 B1 | 10/2003 | Hancock et al. |
| 6,638,245 B2 | 10/2003 | Miller |
| 6,638,293 B1 | 10/2003 | Makower et al. |
| 6,641,590 B1 | 11/2003 | Palmer et al. |
| 6,656,218 B1 | 12/2003 | Denardo et al. |
| 6,660,021 B1 | 12/2003 | Palmer |
| 6,663,650 B2 | 12/2003 | Sepetka |

(56) References Cited

U.S. PATENT DOCUMENTS

| | | |
|---|---|---|
| 6,673,089 B1 | 1/2004 | Yassour |
| 6,685,722 B1 | 2/2004 | Rosenbluth |
| 6,692,504 B2 | 2/2004 | Kurz et al. |
| 6,692,508 B2 | 2/2004 | Wensel |
| 6,692,509 B2 | 2/2004 | Wensel |
| 6,695,858 B1 | 2/2004 | Dubrul et al. |
| 6,702,782 B2 | 3/2004 | Miller |
| 6,712,834 B2 | 3/2004 | Yassour et al. |
| 6,726,701 B2 | 4/2004 | Gilson et al. |
| 6,726,703 B2 | 4/2004 | Broome |
| 6,730,104 B1 | 5/2004 | Sepetka |
| 6,783,528 B2 | 8/2004 | Vincent-Prestigiacomo |
| 6,783,538 B2 | 8/2004 | McGuckin, Jr. et al. |
| 6,824,545 B2 | 11/2004 | Sepetka |
| 6,855,155 B2 | 2/2005 | Denardo et al. |
| 6,878,163 B2 | 4/2005 | Denardo et al. |
| 6,890,340 B2 | 5/2005 | Duane |
| 6,913,612 B2 | 7/2005 | Palmer |
| 6,913,618 B2 | 7/2005 | Denardo et al. |
| 6,939,361 B1 | 9/2005 | Kleshinski |
| 6,953,472 B2 | 10/2005 | Palmer et al. |
| 6,989,019 B2 | 1/2006 | Mazzocchi |
| 6,989,021 B2 | 1/2006 | Bosma et al. |
| 6,994,718 B2 | 2/2006 | Groothuis et al. |
| 7,004,954 B1 | 2/2006 | Voss et al. |
| 7,004,955 B2 | 2/2006 | Shen |
| 7,004,956 B2 | 2/2006 | Palmer |
| 7,008,434 B2 | 3/2006 | Kurz et al. |
| 7,033,376 B2 | 4/2006 | Tsukernik |
| 7,041,116 B2 | 5/2006 | Goto |
| 7,048,758 B2 | 5/2006 | Boyle |
| 7,052,500 B2 | 5/2006 | Bashiri et al. |
| 7,058,456 B2 | 6/2006 | Pierce |
| 7,063,707 B2 | 6/2006 | Bose |
| 7,083,633 B2 | 8/2006 | Morrill et al. |
| 7,083,822 B2 | 8/2006 | Brightbill |
| 7,094,249 B1 | 8/2006 | Broome |
| 7,097,653 B2 | 8/2006 | Freudenthal |
| 7,101,380 B2 | 9/2006 | Khachin |
| 7,172,614 B2 | 2/2007 | Boyle et al. |
| 7,175,655 B1 | 2/2007 | Malaei |
| 7,179,273 B1 | 2/2007 | Palmer et al. |
| 7,185,922 B2 | 3/2007 | Takayanagi et al. |
| 7,220,271 B2 | 5/2007 | Clubb |
| 7,226,464 B2 | 6/2007 | Garner et al. |
| 7,229,472 B2 | 6/2007 | DePalma |
| 7,241,304 B2 | 7/2007 | Boyle et al. |
| 7,288,112 B2 | 10/2007 | Denardo et al. |
| 7,300,458 B2 | 11/2007 | Henkes et al. |
| 7,306,618 B2 | 12/2007 | Demond |
| 7,314,483 B2 | 1/2008 | Landau et al. |
| 7,316,692 B2 | 1/2008 | Huffmaster |
| 7,323,001 B2 | 1/2008 | Clubb |
| 7,331,976 B2 | 2/2008 | McGuckin, Jr. |
| 7,344,550 B2 | 3/2008 | Carrison et al. |
| 7,399,308 B2 | 7/2008 | Barillo et al. |
| 7,410,491 B2 | 8/2008 | Hopkins |
| 7,425,215 B2 | 9/2008 | Boyle |
| 7,452,496 B2 | 11/2008 | Brady et al. |
| 7,491,215 B2 | 2/2009 | Vale |
| 7,491,216 B2 | 2/2009 | Brady |
| 7,510,565 B2 | 3/2009 | Gilson et al. |
| 7,534,252 B2 | 5/2009 | Sepetka |
| 7,556,636 B2 | 7/2009 | Mazzocchi |
| 7,582,111 B2 | 9/2009 | Krolik |
| 7,594,926 B2 | 9/2009 | Linder |
| 7,604,649 B2 | 10/2009 | McGuckin et al. |
| 7,604,650 B2 | 10/2009 | Bergheim |
| 7,609,649 B1 | 10/2009 | Bhandari et al. |
| 7,618,434 B2 | 11/2009 | Santra |
| 7,662,165 B2 | 2/2010 | Gilson et al. |
| 7,670,356 B2 | 3/2010 | Mazzocchi |
| 7,678,123 B2 | 3/2010 | Chanduszko |
| 7,691,121 B2 | 4/2010 | Rosenbluth |
| 7,691,124 B2 | 4/2010 | Balgobin |
| 7,708,770 B2 | 5/2010 | Linder |
| 7,717,929 B2 | 5/2010 | Fallman |
| 7,736,385 B2 | 6/2010 | Agnew |
| 7,758,606 B2 | 7/2010 | Streeter et al. |
| 7,758,611 B2 | 7/2010 | Kato |
| 7,766,934 B2 | 8/2010 | Pal |
| 7,771,452 B2 | 8/2010 | Pal |
| 7,780,694 B2 | 8/2010 | Palmer |
| 7,780,700 B2 | 8/2010 | Frazier et al. |
| 7,811,305 B2 | 10/2010 | Balgobin et al. |
| 7,815,659 B2 | 10/2010 | Conlon et al. |
| 7,819,893 B2 | 10/2010 | Brady |
| 7,828,815 B2 | 11/2010 | Mazzocchi |
| 7,828,816 B2 | 11/2010 | Mazzocchi et al. |
| 7,833,240 B2 | 11/2010 | Okushi et al. |
| 7,842,053 B2 | 11/2010 | Chanduszko et al. |
| 7,846,176 B2 | 11/2010 | Mazzocchi |
| 7,846,175 B2 | 12/2010 | Bonnette et al. |
| 7,850,708 B2 | 12/2010 | Pal |
| 7,883,516 B2 | 2/2011 | Huang et al. |
| 7,887,560 B2 | 2/2011 | Kusleika |
| 7,901,426 B2 | 3/2011 | Gilson et al. |
| 7,914,549 B2 | 3/2011 | Morsi |
| 7,922,732 B2 | 4/2011 | Mazzocchi |
| 7,927,784 B2 | 4/2011 | Simpson |
| 7,931,659 B2 | 4/2011 | Bose et al. |
| 7,998,165 B2 | 8/2011 | Huffmaster |
| 8,002,822 B2 | 8/2011 | Glocker et al. |
| 8,021,379 B2 | 9/2011 | Thompson et al. |
| 8,021,380 B2 | 9/2011 | Thompson et al. |
| 8,043,326 B2 | 10/2011 | Hancock et al. |
| 8,048,151 B2 | 11/2011 | O'Brien et al. |
| 8,052,640 B2 | 11/2011 | Fiorella et al. |
| 8,057,497 B1 | 11/2011 | Raju et al. |
| 8,057,507 B2 | 11/2011 | Horan |
| 8,066,757 B2 | 11/2011 | Ferrera et al. |
| 8,070,791 B2 | 12/2011 | Ferrera et al. |
| 8,088,140 B2 | 1/2012 | Ferrera |
| 8,100,935 B2 | 1/2012 | Rosenbluth et al. |
| 8,109,941 B2 | 2/2012 | Richardson |
| 8,118,829 B2 | 2/2012 | Carrison et al. |
| 8,118,856 B2 | 2/2012 | Schreck et al. |
| 8,123,769 B2 | 2/2012 | Osborne |
| 8,137,376 B2 | 3/2012 | Clubb et al. |
| 8,137,377 B2 | 3/2012 | Palmer et al. |
| 8,142,422 B2 | 3/2012 | Makower et al. |
| 8,142,442 B2 | 3/2012 | Palmer et al. |
| 8,182,508 B2 | 5/2012 | Magnuson et al. |
| 8,187,298 B2 | 5/2012 | Pal |
| 8,246,641 B2 | 8/2012 | Osborne et al. |
| 8,246,672 B2 | 8/2012 | Osborne |
| 8,252,017 B2 | 8/2012 | Paul, Jr. et al. |
| 8,252,018 B2 | 8/2012 | Valaie |
| 8,262,689 B2 | 9/2012 | Schneiderman |
| 8,282,668 B2 | 10/2012 | McGuckin, Jr. et al. |
| 8,287,538 B2 | 10/2012 | Brenzel et al. |
| 8,298,257 B2 | 10/2012 | Sepetka et al. |
| RE43,882 E | 12/2012 | Hopkins et al. |
| 8,357,178 B2 | 1/2013 | Grandfield et al. |
| 8,357,179 B2 | 1/2013 | Grandfield et al. |
| 8,357,180 B2 | 1/2013 | Feller, III |
| 8,357,893 B2 | 1/2013 | Xu et al. |
| 8,361,095 B2 | 1/2013 | Osborne |
| 8,361,110 B2 | 1/2013 | Chanduszko |
| 8,366,663 B2 | 2/2013 | Fiorella et al. |
| 8,409,215 B2 | 4/2013 | Sepetka et al. |
| 8,414,482 B2 | 4/2013 | Belson |
| 8,414,543 B2 | 4/2013 | McGuckin, Jr. |
| 8,419,748 B2 | 4/2013 | Valaie |
| 8,460,312 B2 | 6/2013 | Bose et al. |
| 8,460,313 B2 | 6/2013 | Huffmaster |
| 8,486,104 B2 | 7/2013 | Samson et al. |
| 8,512,352 B2 | 8/2013 | Martin |
| 8,529,596 B2 | 9/2013 | Grandfield et al. |
| 8,545,526 B2 | 10/2013 | Martin et al. |
| 8,574,262 B2 | 11/2013 | Ferrera et al. |
| 8,574,915 B2 | 11/2013 | Zhang et al. |
| 8,579,915 B2 | 11/2013 | French et al. |
| 8,585,713 B2 | 11/2013 | Ferrera et al. |

(56) References Cited

U.S. PATENT DOCUMENTS

| | | |
|---|---|---|
| 8,608,761 B2 | 12/2013 | Osborne et al. |
| 8,679,142 B2 | 3/2014 | Slee et al. |
| 8,690,907 B1 | 4/2014 | Janardhan et al. |
| 8,696,622 B2 | 4/2014 | Fiorella et al. |
| 8,702,652 B2 | 4/2014 | Fiorella et al. |
| 8,702,704 B2 | 4/2014 | Shelton, IV et al. |
| 8,702,724 B2 | 4/2014 | Olsen et al. |
| 8,777,919 B2 | 7/2014 | Kimura et al. |
| 8,777,976 B2 | 7/2014 | Brady et al. |
| 8,777,979 B2 | 7/2014 | Shrivastava et al. |
| 8,784,434 B2 | 7/2014 | Rosenbluth et al. |
| 8,784,441 B2 | 7/2014 | Rosenbluth et al. |
| 8,795,305 B2 | 8/2014 | Grandfield et al. |
| 8,795,317 B2 | 8/2014 | Grandfield et al. |
| 8,795,345 B2 | 8/2014 | Grandfield et al. |
| 8,814,892 B2 | 8/2014 | Galdonik et al. |
| 8,814,925 B2 | 8/2014 | Hilaire et al. |
| 8,852,205 B2 | 10/2014 | Brady et al. |
| 8,870,941 B2 | 10/2014 | Evans et al. |
| 8,900,265 B1 | 12/2014 | Ulm, III |
| 8,920,358 B2 | 12/2014 | Levine et al. |
| 8,939,991 B2 | 1/2015 | Krolick et al. |
| 8,945,143 B2 | 2/2015 | Ferrera et al. |
| 8,945,160 B2 | 2/2015 | Krolik et al. |
| 8,945,169 B2 | 2/2015 | Pal |
| 8,945,172 B2 | 2/2015 | Ferrera et al. |
| 8,956,399 B2 | 2/2015 | Cam et al. |
| 8,968,330 B2 | 3/2015 | Rosenbluth et al. |
| 9,011,481 B2 | 4/2015 | Aggerholm et al. |
| 9,039,749 B2 | 5/2015 | Shrivastava et al. |
| 9,072,537 B2 | 7/2015 | Grandfield |
| 9,095,342 B2 | 8/2015 | Becking et al. |
| 9,113,936 B2 | 8/2015 | Palmer et al. |
| 9,119,656 B2 | 9/2015 | Bose et al. |
| 9,138,307 B2 | 9/2015 | Valaie |
| 9,155,552 B2 | 10/2015 | Ulm, III |
| 9,161,758 B2 | 10/2015 | Figulla |
| 9,161,766 B2 | 10/2015 | Slee et al. |
| 9,173,668 B2 | 11/2015 | Ulm, III |
| 9,173,688 B2 | 11/2015 | Dosta |
| 9,186,487 B2 | 11/2015 | Dubrul et al. |
| 9,198,687 B2 | 12/2015 | Fulkerson et al. |
| 9,204,887 B2 | 12/2015 | Cully et al. |
| 9,221,132 B2 | 12/2015 | Bowman |
| 9,232,992 B2 | 1/2016 | Heidner |
| 9,254,371 B2 | 2/2016 | Martin et al. |
| 9,301,769 B2 | 4/2016 | Brady et al. |
| 9,332,999 B2 | 5/2016 | Ray et al. |
| 9,402,707 B2 | 8/2016 | Brady et al. |
| 9,445,829 B2 | 9/2016 | Brady et al. |
| 9,456,834 B2 | 10/2016 | Folk |
| 9,532,792 B2 | 1/2017 | Galdonik et al. |
| 9,532,873 B2 | 1/2017 | Kelley |
| 9,533,344 B2 | 1/2017 | Monetti et al. |
| 9,539,011 B2 | 1/2017 | Chen et al. |
| 9,539,022 B2 | 1/2017 | Bowman |
| 9,539,122 B2 | 1/2017 | Burke et al. |
| 9,539,382 B2 | 1/2017 | Nelson |
| 9,549,830 B2 | 1/2017 | Bruszewski et al. |
| 9,554,805 B2 | 1/2017 | Tompkins et al. |
| 9,561,125 B2 | 2/2017 | Bowman et al. |
| 9,572,982 B2 | 2/2017 | Burnes et al. |
| 9,579,104 B2 | 2/2017 | Beckham et al. |
| 9,579,484 B2 | 2/2017 | Barnell |
| 9,585,642 B2 | 3/2017 | Dinsmoor et al. |
| 9,615,832 B2 | 4/2017 | Bose et al. |
| 9,615,951 B2 | 4/2017 | Bennett et al. |
| 9,622,753 B2 | 4/2017 | Cox |
| 9,636,115 B2 | 5/2017 | Henry et al. |
| 9,636,439 B2 | 5/2017 | Chu et al. |
| 9,642,639 B2 | 5/2017 | Brady et al. |
| 9,642,675 B2 | 5/2017 | Werneth et al. |
| 9,655,633 B2 | 5/2017 | Leynov et al. |
| 9,655,645 B2 | 5/2017 | Staunton |
| 9,655,898 B2 | 5/2017 | Palepu et al. |
| 9,655,989 B2 | 5/2017 | Cruise et al. |
| 9,662,129 B2 | 5/2017 | Galdonik et al. |
| 9,662,238 B2 | 5/2017 | Dwork et al. |
| 9,662,425 B2 | 5/2017 | Lilja et al. |
| 9,668,898 B2 | 6/2017 | Wong |
| 9,675,477 B2 | 6/2017 | Thompson |
| 9,675,782 B2 | 6/2017 | Connolly |
| 9,676,022 B2 | 6/2017 | Ensign et al. |
| 9,692,557 B2 | 6/2017 | Murphy |
| 9,693,852 B2 | 7/2017 | Lam et al. |
| 9,700,262 B2 | 7/2017 | Janik et al. |
| 9,700,399 B2 | 7/2017 | Acosta-Acevedo |
| 9,717,421 B2 | 8/2017 | Griswold et al. |
| 9,717,500 B2 | 8/2017 | Tieu et al. |
| 9,717,502 B2 | 8/2017 | Teoh et al. |
| 9,724,103 B2 | 8/2017 | Cruise et al. |
| 9,724,526 B2 | 8/2017 | Strother et al. |
| 9,750,565 B2 | 9/2017 | Bloom et al. |
| 9,757,260 B2 | 9/2017 | Greenan |
| 9,758,606 B2 | 9/2017 | Lambert et al. |
| 9,764,111 B2 | 9/2017 | Gulachenski |
| 9,770,251 B2 | 9/2017 | Bowman et al. |
| 9,770,577 B2 | 9/2017 | Li et al. |
| 9,775,621 B2 | 10/2017 | Tompkins et al. |
| 9,775,706 B2 | 10/2017 | Peterson et al. |
| 9,775,732 B2 | 10/2017 | Khenansho |
| 9,788,800 B2 | 10/2017 | Mayoras, Jr. |
| 9,795,391 B2 | 10/2017 | Saatchi et al. |
| 9,801,980 B2 | 10/2017 | Karino et al. |
| 9,808,599 B2 | 11/2017 | Bowman et al. |
| 9,833,252 B2 | 12/2017 | Sepetka et al. |
| 9,833,304 B2 | 12/2017 | Horan |
| 9,833,604 B2 | 12/2017 | Lam et al. |
| 9,833,625 B2 | 12/2017 | Waldhauser et al. |
| 9,901,434 B2 | 2/2018 | Hoffman |
| 9,918,720 B2 | 3/2018 | Marchand et al. |
| 9,939,361 B2 | 4/2018 | Gajji et al. |
| 10,070,878 B2 | 9/2018 | Ma |
| 10,201,360 B2 | 2/2019 | Vale et al. |
| 10,231,751 B2 | 3/2019 | Sos |
| 10,292,723 B2 | 5/2019 | Brady et al. |
| 10,299,811 B2 | 5/2019 | Brady et al. |
| 10,363,054 B2 | 7/2019 | Vale et al. |
| 10,376,274 B2 | 8/2019 | Farin et al. |
| 10,390,850 B2 | 8/2019 | Vale et al. |
| 10,524,811 B2 | 1/2020 | Marchand et al. |
| 10,617,435 B2 | 4/2020 | Vale et al. |
| 10,722,257 B2 | 7/2020 | Skillrud et al. |
| 2001/0001315 A1 | 5/2001 | Bates |
| 2001/0016755 A1 | 8/2001 | Addis |
| 2001/0037141 A1 | 11/2001 | Yee et al. |
| 2001/0037171 A1 | 11/2001 | Sato |
| 2001/0041909 A1 | 11/2001 | Tsugita et al. |
| 2001/0049554 A1 | 12/2001 | Ruiz et al. |
| 2001/0051810 A1 | 12/2001 | Dubrul |
| 2002/0004667 A1 | 1/2002 | Adams |
| 2002/0016609 A1 | 2/2002 | Wensel |
| 2002/0022859 A1 | 2/2002 | Hogendijk |
| 2002/0026211 A1 | 2/2002 | Khosravi |
| 2002/0042627 A1 | 4/2002 | Brady et al. |
| 2002/0049468 A1 | 4/2002 | Streeter |
| 2002/0052620 A1 | 5/2002 | Barbut |
| 2002/0058911 A1 | 5/2002 | Gilson et al. |
| 2002/0068954 A1 | 6/2002 | Foster |
| 2002/0072764 A1 | 6/2002 | Sepetka |
| 2002/0082558 A1 | 6/2002 | Samson |
| 2002/0091407 A1 | 7/2002 | Zadno-Azizi et al. |
| 2002/0095171 A1 | 7/2002 | Belef |
| 2002/0123765 A1 | 9/2002 | Sepetka |
| 2002/0138094 A1 | 9/2002 | Borillo et al. |
| 2002/0143349 A1 | 10/2002 | Gifford, III et al. |
| 2002/0143362 A1 | 10/2002 | Macoviak |
| 2002/0156455 A1 | 10/2002 | Barbut |
| 2002/0161393 A1 | 10/2002 | Demond |
| 2002/0165576 A1 | 11/2002 | Boyle et al. |
| 2002/0173819 A1 | 11/2002 | Leeflang et al. |
| 2002/0183787 A1 | 12/2002 | Wahr et al. |
| 2002/0188276 A1 | 12/2002 | Evans |
| 2002/0188314 A1 | 12/2002 | Anderson et al. |

(56) References Cited

U.S. PATENT DOCUMENTS

| | | |
|---|---|---|
| 2002/0193824 A1 | 12/2002 | Boylan et al. |
| 2002/0198588 A1 | 12/2002 | Armstrong et al. |
| 2003/0004536 A1 | 1/2003 | Boylan |
| 2003/0004538 A1 | 1/2003 | Secrest |
| 2003/0004540 A1 | 1/2003 | Linder |
| 2003/0004542 A1 | 1/2003 | Wensel |
| 2003/0009146 A1 | 1/2003 | Muni |
| 2003/0009191 A1 | 1/2003 | Wensel |
| 2003/0038447 A1 | 2/2003 | Cantele |
| 2003/0040772 A1 | 2/2003 | Hyodoh |
| 2003/0050663 A1 | 3/2003 | Khachin |
| 2003/0064151 A1 | 4/2003 | Klinedinst |
| 2003/0108224 A1 | 6/2003 | Ike |
| 2003/0114879 A1 | 6/2003 | Euteneuer |
| 2003/0125798 A1 | 7/2003 | Martin |
| 2003/0130682 A1 | 7/2003 | Broome |
| 2003/0144687 A1 | 7/2003 | Brady et al. |
| 2003/0144688 A1 | 7/2003 | Brady et al. |
| 2003/0153158 A1 | 8/2003 | Ho et al. |
| 2003/0153943 A1 | 8/2003 | Michael |
| 2003/0153944 A1 | 8/2003 | Phung |
| 2003/0163064 A1 | 8/2003 | Vrba |
| 2003/0163158 A1 | 8/2003 | White |
| 2003/0171769 A1 | 9/2003 | Barbut |
| 2003/0171771 A1 | 9/2003 | Anderson et al. |
| 2003/0176884 A1 | 9/2003 | Berrada |
| 2003/0187495 A1 | 10/2003 | Cully et al. |
| 2003/0195537 A1 | 10/2003 | Dubrul |
| 2003/0195554 A1 | 10/2003 | Shen |
| 2003/0199917 A1 | 10/2003 | Knudson |
| 2003/0204202 A1 | 10/2003 | Palmer |
| 2003/0208224 A1 | 11/2003 | Broome |
| 2003/0212430 A1 | 11/2003 | Bose |
| 2003/0236533 A1 | 12/2003 | Wilson |
| 2004/0064179 A1 | 4/2004 | Linder et al. |
| 2004/0068288 A1 | 4/2004 | Palmer et al. |
| 2004/0073243 A1 | 4/2004 | Sepetka |
| 2004/0079429 A1 | 4/2004 | Miller |
| 2004/0082962 A1 | 4/2004 | Demarais et al. |
| 2004/0082967 A1 | 4/2004 | Broome et al. |
| 2004/0088001 A1 | 5/2004 | Bosma |
| 2004/0093065 A1 | 5/2004 | Yachia |
| 2004/0098050 A1 | 5/2004 | Foerster et al. |
| 2004/0133231 A1 | 7/2004 | Maitland |
| 2004/0133232 A1 | 7/2004 | Rosenbluth et al. |
| 2004/0138692 A1 | 7/2004 | Phung |
| 2004/0153117 A1 | 8/2004 | Clubb et al. |
| 2004/0153118 A1 | 8/2004 | Clubb |
| 2004/0199201 A1 | 10/2004 | Kellett et al. |
| 2004/0215318 A1 | 10/2004 | Kwitkin |
| 2004/0220663 A1 | 11/2004 | Rivelli |
| 2005/0033248 A1 | 2/2005 | Machida et al. |
| 2005/0033348 A1 | 2/2005 | Sepetka |
| 2005/0038447 A1 | 2/2005 | Huffmaster |
| 2005/0038468 A1 | 2/2005 | Panetta |
| 2005/0043759 A1 | 2/2005 | Chanduszko |
| 2005/0049619 A1 | 3/2005 | Sepetka |
| 2005/0049669 A1 | 3/2005 | Jones |
| 2005/0049670 A1 | 3/2005 | Jones et al. |
| 2005/0055033 A1 | 3/2005 | Leslie et al. |
| 2005/0055047 A1 | 3/2005 | Greenhalgh |
| 2005/0058837 A1 | 3/2005 | Farnworth |
| 2005/0059995 A1 | 3/2005 | Sepetka |
| 2005/0085849 A1 | 4/2005 | Sepetka |
| 2005/0090779 A1 | 4/2005 | Osypka |
| 2005/0090857 A1 | 4/2005 | Kusleika et al. |
| 2005/0125024 A1 | 6/2005 | Sepetka |
| 2005/0149997 A1 | 7/2005 | Wolozin et al. |
| 2005/0171566 A1 | 8/2005 | Kanamaru |
| 2005/0173135 A1 | 8/2005 | Almen |
| 2005/0192627 A1 | 9/2005 | Whisenant et al. |
| 2005/0216030 A1 | 9/2005 | Sepetka |
| 2005/0216050 A1 | 9/2005 | Sepetka |
| 2005/0228417 A1 | 10/2005 | Teitelbaum et al. |
| 2005/0251206 A1 | 11/2005 | Maahs et al. |
| 2005/0251209 A1 | 11/2005 | Saadat et al. |
| 2005/0267491 A1 | 12/2005 | Kellett et al. |
| 2005/0273135 A1 | 12/2005 | Chanduszko et al. |
| 2005/0283186 A1 | 12/2005 | Berrada et al. |
| 2005/0288686 A1 | 12/2005 | Sepetka |
| 2006/0008332 A1 | 1/2006 | Greenberg et al. |
| 2006/0009798 A1 | 1/2006 | Callister et al. |
| 2006/0009799 A1 | 1/2006 | Kleshinski |
| 2006/0020286 A1 | 1/2006 | Niermann |
| 2006/0030877 A1 | 2/2006 | Martinez |
| 2006/0041228 A1 | 2/2006 | Vo et al. |
| 2006/0058836 A1 | 3/2006 | Bose |
| 2006/0058837 A1 | 3/2006 | Bose et al. |
| 2006/0058838 A1 | 3/2006 | Bose |
| 2006/0064151 A1 | 3/2006 | Guterman |
| 2006/0069424 A1 | 3/2006 | Acosta et al. |
| 2006/0074477 A1 | 4/2006 | Berthiaume et al. |
| 2006/0149313 A1 | 7/2006 | Arguello et al. |
| 2006/0155305 A1 | 7/2006 | Freudenthal |
| 2006/0161187 A1 | 7/2006 | Levine |
| 2006/0195137 A1 | 8/2006 | Sepetka |
| 2006/0224177 A1 | 10/2006 | Finitsis |
| 2006/0224179 A1 | 10/2006 | Kucharczyk |
| 2006/0229638 A1 | 10/2006 | Abrams et al. |
| 2006/0235501 A1 | 10/2006 | Igaki |
| 2006/0241677 A1 | 10/2006 | Johnson et al. |
| 2006/0282111 A1 | 12/2006 | Morsi |
| 2006/0287668 A1 | 12/2006 | Fawzi et al. |
| 2006/0287701 A1 | 12/2006 | Pal |
| 2006/0293706 A1 | 12/2006 | Shimon |
| 2007/0010857 A1 | 1/2007 | Sugimoto et al. |
| 2007/0032879 A1 | 2/2007 | Levine et al. |
| 2007/0088382 A1 | 4/2007 | Bei et al. |
| 2007/0088383 A1 | 4/2007 | Pal et al. |
| 2007/0100348 A1 | 5/2007 | Cauthen, III et al. |
| 2007/0118173 A1 | 5/2007 | Magnuson et al. |
| 2007/0149997 A1 | 6/2007 | Muller |
| 2007/0156170 A1 | 7/2007 | Hancock |
| 2007/0165170 A1 | 7/2007 | Fukuda |
| 2007/0179527 A1 | 8/2007 | Eskuri et al. |
| 2007/0191866 A1 | 8/2007 | Palmer et al. |
| 2007/0198028 A1 | 8/2007 | Miloslavski |
| 2007/0198051 A1 | 8/2007 | Clubb et al. |
| 2007/0198075 A1 | 8/2007 | Levy |
| 2007/0208367 A1 | 9/2007 | Fiorella |
| 2007/0208371 A1 | 9/2007 | French |
| 2007/0225749 A1 | 9/2007 | Martin |
| 2007/0233175 A1 | 10/2007 | Zaver et al. |
| 2007/0244505 A1 | 10/2007 | Gilson et al. |
| 2007/0270902 A1 | 11/2007 | Slazas |
| 2007/0288054 A1 | 12/2007 | Tanaka |
| 2008/0045881 A1 | 2/2008 | Teitelbaum et al. |
| 2008/0077227 A1 | 3/2008 | Ouellette et al. |
| 2008/0082107 A1 | 4/2008 | Miller et al. |
| 2008/0086190 A1 | 4/2008 | Ta |
| 2008/0091223 A1 | 4/2008 | Pokorney |
| 2008/0097386 A1 | 4/2008 | Osypka |
| 2008/0109031 A1 | 5/2008 | Sepetka |
| 2008/0109032 A1 | 5/2008 | Sepetka |
| 2008/0119886 A1 | 5/2008 | Greenhalgh et al. |
| 2008/0177296 A1 | 7/2008 | Sepetka |
| 2008/0178890 A1 | 7/2008 | Townsend et al. |
| 2008/0183197 A1 | 7/2008 | Sepetka |
| 2008/0183198 A1 | 7/2008 | Sepetka |
| 2008/0183205 A1 | 7/2008 | Sepetka |
| 2008/0188876 A1 | 8/2008 | Sepetka |
| 2008/0188885 A1 | 8/2008 | Sepetka |
| 2008/0188887 A1 | 8/2008 | Batiste |
| 2008/0200946 A1 | 8/2008 | Braun |
| 2008/0200947 A1 | 8/2008 | Kusleika et al. |
| 2008/0215077 A1 | 9/2008 | Sepetka |
| 2008/0221600 A1 | 9/2008 | Dieck |
| 2008/0228209 A1 | 9/2008 | DeMello et al. |
| 2008/0234706 A1 | 9/2008 | Sepetka |
| 2008/0243170 A1 | 10/2008 | Jenson |
| 2008/0255596 A1 | 10/2008 | Jenson |
| 2008/0262410 A1 | 10/2008 | Jenson et al. |
| 2008/0262528 A1 | 10/2008 | Martin |
| 2008/0262532 A1 | 10/2008 | Martin |

(56) References Cited

U.S. PATENT DOCUMENTS

| | | |
|---|---|---|
| 2008/0269871 A1 | 10/2008 | Eli |
| 2008/0275488 A1 | 11/2008 | Fleming |
| 2008/0275493 A1 | 11/2008 | Farmiga |
| 2008/0281350 A1 | 11/2008 | Sepetka |
| 2008/0312681 A1 | 12/2008 | Ansel |
| 2009/0005858 A1 | 1/2009 | Young et al. |
| 2009/0024157 A1 | 1/2009 | Anukhin |
| 2009/0030443 A1 | 1/2009 | Buser et al. |
| 2009/0062841 A1 | 3/2009 | Amplatz et al. |
| 2009/0069828 A1 | 3/2009 | Martin |
| 2009/0076539 A1 | 3/2009 | Valaie |
| 2009/0088793 A1 | 4/2009 | Bagaoisan et al. |
| 2009/0088795 A1 | 4/2009 | Cahill |
| 2009/0105722 A1 | 4/2009 | Fulkerson |
| 2009/0105737 A1 | 4/2009 | Fulkerson |
| 2009/0105747 A1 | 4/2009 | Chanduszko et al. |
| 2009/0149881 A1 | 6/2009 | Vale et al. |
| 2009/0163851 A1 | 6/2009 | Holloway et al. |
| 2009/0177206 A1 | 7/2009 | Lozier |
| 2009/0182336 A1 | 7/2009 | Brenzel |
| 2009/0281610 A1 | 11/2009 | Parker |
| 2009/0281619 A1 | 11/2009 | Le et al. |
| 2009/0292297 A1 | 11/2009 | Ferrere |
| 2009/0292307 A1 | 11/2009 | Razack |
| 2009/0299393 A1 | 12/2009 | Martin |
| 2009/0299403 A1 | 12/2009 | Chanduszko |
| 2009/0306702 A1 | 12/2009 | Miloslavski |
| 2009/0326636 A1 | 12/2009 | Hashimoto et al. |
| 2010/0004607 A1 | 1/2010 | Wilson et al. |
| 2010/0076482 A1 | 3/2010 | Shu et al. |
| 2010/0087850 A1 | 4/2010 | Razack |
| 2010/0087908 A1 | 4/2010 | Hilaire |
| 2010/0114017 A1 | 5/2010 | Lenker |
| 2010/0125326 A1 | 5/2010 | Kalstad |
| 2010/0125327 A1 | 5/2010 | Agnew |
| 2010/0191272 A1 | 7/2010 | Keating |
| 2010/0211094 A1 | 8/2010 | Sargent, Jr. |
| 2010/0268264 A1 | 10/2010 | Bonnett et al. |
| 2010/0268265 A1 | 10/2010 | Krolik et al. |
| 2010/0274277 A1 | 10/2010 | Eaton |
| 2010/0318178 A1 | 12/2010 | Rapaport et al. |
| 2010/0324649 A1 | 12/2010 | Mattsson |
| 2010/0331949 A1 | 12/2010 | Habib |
| 2011/0009875 A1 | 1/2011 | Grandfield et al. |
| 2011/0009940 A1 | 1/2011 | Grandfield |
| 2011/0009950 A1 | 1/2011 | Grandfield et al. |
| 2011/0022149 A1 | 1/2011 | Cox |
| 2011/0040319 A1 | 2/2011 | Fulton, III |
| 2011/0054514 A1 | 3/2011 | Arcand |
| 2011/0054516 A1 | 3/2011 | Keegan |
| 2011/0060212 A1 | 3/2011 | Slee et al. |
| 2011/0060359 A1 | 3/2011 | Hannes |
| 2011/0054504 A1 | 5/2011 | Wolf et al. |
| 2011/0106137 A1 | 5/2011 | Shimon |
| 2011/0125181 A1 | 5/2011 | Brady et al. |
| 2011/0152920 A1 | 6/2011 | Eckhouse et al. |
| 2011/0160763 A1 | 6/2011 | Ferrera |
| 2011/0166586 A1 | 7/2011 | Sepetka et al. |
| 2011/0184456 A1 | 7/2011 | Grandfield et al. |
| 2011/0196414 A1 | 8/2011 | Porter et al. |
| 2011/0202088 A1 | 8/2011 | Eckhouse et al. |
| 2011/0208233 A1 | 8/2011 | McGuckin, Jr. et al. |
| 2011/0213297 A1 | 9/2011 | Aklog et al. |
| 2011/0213393 A1 | 9/2011 | Aklog et al. |
| 2011/0213403 A1 | 9/2011 | Aboytes |
| 2011/0224707 A1 | 9/2011 | Miloslavski |
| 2011/0276120 A1 | 11/2011 | Gilson et al. |
| 2011/0319917 A1 | 12/2011 | Ferrera et al. |
| 2012/0041449 A1 | 2/2012 | Eckhouse et al. |
| 2012/0041474 A1 | 2/2012 | Eckhouse et al. |
| 2012/0059356 A1 | 3/2012 | diPalma et al. |
| 2012/0065660 A1 | 3/2012 | Ferrera et al. |
| 2012/0083823 A1 | 4/2012 | Shrivastava |
| 2012/0083868 A1 | 4/2012 | Shrivastava et al. |
| 2012/0089216 A1 | 4/2012 | Rapaport et al. |
| 2012/0101510 A1 | 4/2012 | Lenker et al. |
| 2012/0123466 A1 | 5/2012 | Porter et al. |
| 2012/0022572 A1 | 6/2012 | Braun et al. |
| 2012/0150147 A1 | 6/2012 | Leynov et al. |
| 2012/0165858 A1 | 6/2012 | Eckhouse et al. |
| 2012/0165859 A1 | 6/2012 | Eckhouse et al. |
| 2012/0296362 A1 | 6/2012 | Cam |
| 2012/0209312 A1 | 8/2012 | Aggerholm et al. |
| 2012/0215250 A1 | 8/2012 | Grandfield et al. |
| 2012/0143237 A1 | 11/2012 | Cam |
| 2012/0277788 A1 | 11/2012 | Cattaneo |
| 2012/0283768 A1 | 11/2012 | Cox et al. |
| 2012/0316600 A1 | 12/2012 | Ferrera et al. |
| 2012/0330350 A1 | 12/2012 | Jones et al. |
| 2013/0030460 A1 | 1/2013 | Marks et al. |
| 2013/0030461 A1 | 1/2013 | Marks et al. |
| 2013/0046330 A1 | 2/2013 | McIntosh |
| 2013/0046333 A1 | 2/2013 | Jones et al. |
| 2013/0046334 A1 | 2/2013 | Jones et al. |
| 2013/0116774 A1 | 5/2013 | Strauss |
| 2013/0131614 A1 | 5/2013 | Hassan et al. |
| 2013/0144311 A1 | 6/2013 | Fung et al. |
| 2013/0144326 A1 | 6/2013 | Brady et al. |
| 2013/0158592 A1 | 6/2013 | Porter |
| 2013/0184739 A1 | 7/2013 | Brady et al. |
| 2013/0197567 A1 | 8/2013 | Brady et al. |
| 2013/0226146 A1 | 8/2013 | Tekulve |
| 2013/0268050 A1 | 10/2013 | Wilson et al. |
| 2013/0271788 A1 | 10/2013 | Utsunomiya |
| 2013/0277079 A1 | 10/2013 | Tsuzuki et al. |
| 2013/0281788 A1 | 10/2013 | Garrison |
| 2013/0325051 A1 | 12/2013 | Martin et al. |
| 2013/0325055 A1 | 12/2013 | Eckhouse et al. |
| 2013/0325056 A1 | 12/2013 | Eckhouse et al. |
| 2013/0345739 A1 | 12/2013 | Brady et al. |
| 2014/0005712 A1 | 1/2014 | Martin |
| 2014/0005713 A1 | 1/2014 | Bowman |
| 2014/0046359 A1 | 2/2014 | Bowman et al. |
| 2014/0121672 A1 | 5/2014 | Folk |
| 2014/0128905 A1 | 5/2014 | Molaei |
| 2014/0134654 A1 | 5/2014 | Rudel et al. |
| 2014/0135812 A1 | 5/2014 | Divino et al. |
| 2014/0142598 A1 | 5/2014 | Fulton, III |
| 2014/0180377 A1 | 6/2014 | Bose et al. |
| 2014/0180397 A1 | 6/2014 | Gerberding et al. |
| 2014/0183077 A1 | 7/2014 | Rosendall et al. |
| 2014/0194911 A1 | 7/2014 | Johnson et al. |
| 2014/0194919 A1 | 7/2014 | Losardo et al. |
| 2014/0200607 A1 | 7/2014 | Sepetka et al. |
| 2014/0200608 A1 | 7/2014 | Brady et al. |
| 2014/0236220 A1 | 8/2014 | Inoue |
| 2014/0243881 A1 | 8/2014 | Lees et al. |
| 2014/0257362 A1 | 9/2014 | Eidenschink |
| 2014/0276922 A1 | 9/2014 | McLain et al. |
| 2014/0277079 A1 | 9/2014 | Vale et al. |
| 2014/0303667 A1 | 10/2014 | Cox et al. |
| 2014/0309657 A1 | 10/2014 | Ben-Ami |
| 2014/0309673 A1 | 10/2014 | Dacuycuy et al. |
| 2014/0330302 A1 | 11/2014 | Tekulve et al. |
| 2014/0343585 A1 | 11/2014 | Ferrera et al. |
| 2014/0371769 A1 | 12/2014 | Vale et al. |
| 2014/0371779 A1 | 12/2014 | Vale et al. |
| 2014/0371780 A1 | 12/2014 | Vale et al. |
| 2014/0372779 A1 | 12/2014 | Wong et al. |
| 2014/0379023 A1 | 12/2014 | Brady et al. |
| 2015/0018859 A1 | 1/2015 | Quick et al. |
| 2015/0018860 A1 | 1/2015 | Quick et al. |
| 2015/0032144 A1 | 1/2015 | Holloway |
| 2015/0080937 A1 | 3/2015 | Davidson |
| 2015/0112376 A1 | 4/2015 | Molaei et al. |
| 2015/0133990 A1 | 5/2015 | Davidson |
| 2015/0150672 A1 | 6/2015 | Ma |
| 2015/0164523 A1 | 6/2015 | Brady et al. |
| 2015/0224133 A1 | 8/2015 | Ohri et al. |
| 2015/0250497 A1 | 9/2015 | Marks et al. |
| 2015/0257775 A1 | 9/2015 | Gilvarry et al. |
| 2015/0272716 A1 | 10/2015 | Pinchuk et al. |
| 2015/0297252 A1 | 10/2015 | Miloslavski et al. |
| 2015/0313617 A1 | 11/2015 | Grandfield et al. |

(56) References Cited

U.S. PATENT DOCUMENTS

| | | |
|---|---|---|
| 2015/0320431 A1 | 11/2015 | Ulm, III |
| 2015/0352325 A1 | 12/2015 | Quick |
| 2015/0359547 A1 | 12/2015 | Vale et al. |
| 2015/0366650 A1 | 12/2015 | Zi et al. |
| 2015/0374391 A1 | 12/2015 | Quick et al. |
| 2015/0374393 A1 | 12/2015 | Brady et al. |
| 2015/0374479 A1 | 12/2015 | Vale |
| 2016/0015402 A1 | 1/2016 | Brady et al. |
| 2016/0022269 A1 | 1/2016 | Ganske et al. |
| 2016/0022296 A1 | 1/2016 | Brady et al. |
| 2016/0045298 A1 | 2/2016 | Thinnes, Jr. et al. |
| 2016/0066921 A1 | 3/2016 | Brady et al. |
| 2016/0100928 A1 | 4/2016 | Lees et al. |
| 2016/0106448 A1 | 4/2016 | Seifert et al. |
| 2016/0106449 A1 | 4/2016 | Brady et al. |
| 2016/0113663 A1 | 4/2016 | Brady et al. |
| 2016/0113664 A1 | 4/2016 | Brady et al. |
| 2016/0113665 A1 | 4/2016 | Brady et al. |
| 2016/0120558 A1 | 5/2016 | Brady et al. |
| 2016/0143653 A1 | 5/2016 | Vale et al. |
| 2016/0192953 A1 | 7/2016 | Brady et al. |
| 2016/0192954 A1 | 7/2016 | Brady et al. |
| 2016/0192955 A1 | 7/2016 | Brady et al. |
| 2016/0192956 A1 | 7/2016 | Brady et al. |
| 2016/0256180 A1 | 9/2016 | Vale et al. |
| 2016/0303381 A1 | 10/2016 | Pierce et al. |
| 2016/0317168 A1 | 11/2016 | Vale et al. |
| 2017/0007264 A1 | 1/2017 | Cruise et al. |
| 2017/0007265 A1 | 1/2017 | Guo et al. |
| 2017/0020542 A1 | 1/2017 | Martin et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0056061 A1 | 3/2017 | Ogle et al. |
| 2017/0071614 A1 | 3/2017 | Vale et al. |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086862 A1 | 3/2017 | Vale et al. |
| 2017/0086863 A1 | 3/2017 | Brady et al. |
| 2017/0086996 A1 | 3/2017 | Peterson et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0105743 A1 | 4/2017 | Vale et al. |
| 2017/0112515 A1 | 4/2017 | Brady et al. |
| 2017/0112647 A1 | 4/2017 | Sachar et al. |
| 2017/0113023 A1 | 4/2017 | Steingisser et al. |
| 2017/0119409 A1 | 5/2017 | Ma |
| 2017/0143465 A1* | 5/2017 | Ulm, III ............... A61F 2/012 |
| 2017/0147765 A1 | 5/2017 | Mehta |
| 2017/0150979 A1 | 6/2017 | Ulm |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0252064 A1 | 9/2017 | Staunton |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2018/0055884 A1 | 3/2018 | Barclay Dupere et al. |
| 2018/0263650 A1 | 9/2018 | Iwanami et al. |
| 2018/0325537 A1 | 11/2018 | Shamay et al. |
| 2018/0326024 A1 | 11/2018 | Prochazka et al. |
| 2018/0344338 A1 | 12/2018 | Brady et al. |
| 2019/0000492 A1 | 1/2019 | Casey et al. |
| 2019/0015061 A1 | 1/2019 | Liebskind et al. |
| 2019/0167284 A1 | 6/2019 | Friedman et al. |
| 2019/0239907 A1 | 8/2019 | Brady et al. |
| 2019/0292273 A1 | 9/2019 | Hanotin et al. |
| 2019/0374239 A1 | 12/2019 | Martin et al. |
| 2019/0380723 A1 | 12/2019 | Grandfield et al. |
| 2019/0388097 A1 | 12/2019 | Girdhar et al. |
| 2020/0009150 A1 | 1/2020 | Chamorro Sanchez |
| 2020/0085444 A1 | 3/2020 | Vale et al. |
| 2020/0100804 A1 | 4/2020 | Casey et al. |

FOREIGN PATENT DOCUMENTS

| | | |
|---|---|---|
| CN | 102307613 A | 1/2012 |
| CN | 102596098 A | 7/2012 |
| CN | 104042304 A | 9/2014 |
| CN | 105208950 A | 12/2015 |
| CN | 105662532 A | 6/2016 |
| CN | 205359559 U | 7/2016 |
| CN | 107530090 A | 1/2018 |
| CN | 208582467 U | 3/2019 |
| DE | 202009001951 U1 | 4/2010 |
| DE | 102009056450 | 6/2011 |
| DE | 102010010849 | 9/2011 |
| DE | 10 2010 014778 A1 | 10/2011 |
| DE | 102010024085 | 12/2011 |
| DE | 102011014586 B3 | 9/2012 |
| EP | 1153581 A1 | 11/2011 |
| EP | 2301450 B1 | 11/2011 |
| EP | 2438891 A1 | 4/2012 |
| EP | 2628455 A1 | 8/2013 |
| EP | 3156004 A1 | 4/2017 |
| GB | 2427554 A | 1/2007 |
| GB | 2494820 A | 3/2013 |
| JP | 9-19438 A | 1/1997 |

(56) References Cited

FOREIGN PATENT DOCUMENTS

| | | |
|---|---|---|
| JP | 2014511223 A | 5/2014 |
| JP | 2014525796 A | 10/2014 |
| JP | 2015-505250 A | 2/2015 |
| JP | 2019-526365 A | 5/2016 |
| JP | 2016-513505 A | 9/2019 |
| VN | 103764049 A | 4/2014 |
| WO | 94/24926 | 11/1994 |
| WO | 97/27808 | 8/1997 |
| WO | 97/38631 A1 | 10/1997 |
| WO | 99/20335 | 4/1999 |
| WO | 99/60933 | 12/1999 |
| WO | 99/56801 | 4/2000 |
| WO | 01/21077 | 3/2001 |
| WO | 2004/056275 A1 | 7/2001 |
| WO | 02/02162 | 1/2002 |
| WO | 02/11627 | 2/2002 |
| WO | 02/43616 | 6/2002 |
| WO | 02/070061 | 9/2002 |
| WO | 02/094111 | 11/2002 |
| WO | 03/002006 | 1/2003 |
| WO | 03/030751 | 4/2003 |
| WO | 03/051448 | 6/2003 |
| WO | 2004/028571 A2 | 4/2004 |
| WO | 2005/000130 A1 | 1/2005 |
| WO | 2005/027779 A2 | 3/2005 |
| WO | 2006/021407 | 3/2006 |
| WO | 2006/031410 | 3/2006 |
| WO | 2006/107641 | 10/2006 |
| WO | 2006/135823 A2 | 12/2006 |
| WO | 2007/054307 | 5/2007 |
| WO | 2007/068424 | 6/2007 |
| WO | 2008/034615 | 3/2008 |
| WO | 2008/051431 A1 | 5/2008 |
| WO | 2008/131116 | 10/2008 |
| WO | 2008135823 A1 | 11/2008 |
| WO | 2009/031338 A1 | 3/2009 |
| WO | 2009/076482 | 6/2009 |
| WO | 2009/086482 | 7/2009 |
| WO | 2009/105710 A1 | 8/2009 |
| WO | 2010/010545 | 1/2010 |
| WO | 2010/046897 A1 | 4/2010 |
| WO | 2010/075565 A2 | 7/2010 |
| WO | 2010/102307 A1 | 9/2010 |
| WO | 2010/146581 A1 | 12/2010 |
| WO | 2011/013556 A1 | 2/2011 |
| WO | 2011/066961 A1 | 6/2011 |
| WO | 2011/082319 A1 | 7/2011 |
| WO | 2011/095352 A1 | 8/2011 |
| WO | 2011/106426 | 9/2011 |
| WO | 2011/110316 A1 | 9/2011 |
| WO | 2011135556 A1 | 11/2011 |
| WO | 2012/052982 A1 | 4/2012 |
| WO | 2012/064726 A1 | 5/2012 |
| WO | 2012/081020 A1 | 6/2012 |
| WO | 2012/120490 A2 | 9/2012 |
| WO | 2012/110619 A9 | 10/2012 |
| WO | 2012/156924 | 11/2012 |
| WO | 2013/016435 A1 | 1/2013 |
| WO | 2013/072777 A2 | 5/2013 |
| WO | 2013/105099 A2 | 7/2013 |
| WO | 2013/109756 A2 | 7/2013 |
| WO | 2013187927 A1 | 12/2013 |
| WO | 2014047650 A1 | 3/2014 |
| WO | 2014/081892 A1 | 5/2014 |
| WO | 2014/139845 A1 | 9/2014 |
| WO | 2014/169266 A1 | 10/2014 |
| WO | 2014/178198 A1 | 11/2014 |
| WO | 2015/061365 A1 | 4/2015 |
| WO | 2015103547 A1 | 7/2015 |
| WO | 2015/134625 A1 | 9/2015 |
| WO | 2015/179324 A2 | 11/2015 |
| WO | 2015/189354 | 12/2015 |
| WO | 2016/010995 A1 | 1/2016 |
| WO | 2016089451 A1 | 6/2016 |
| WO | 2017089424 A1 | 6/2017 |
| WO | WO 2017/161204 A1 | 9/2017 |
| WO | WO 2020/039082 A1 | 2/2020 |
| WO | WO 2021/113302 A1 | 6/2021 |

OTHER PUBLICATIONS

Search Report issued in corresponding Chinese Patent Application No. 201680080064.4 dated Jun. 9, 2020 (English translation only).
US 6,348,062, 07/2003, Hopkins et al. (withdrawn)

* cited by examiner

CLOT RETRIEVAL DEVICE FOR REMOVING CLOT FROM A BLOOD VESSEL

FIELD

The present disclosure generally relates to devices and methods for removing blockages from blood vessels during intravascular medical treatments.

BACKGROUND

Clot retrieval devices are used in mechanical thrombectomy for endovascular intervention, often in cases where patients are suffering from conditions such as acute ischemic stroke (AIS), myocardial infarction (MI), and pulmonary embolism (PE). Acute obstructions may include clot, misplaced devices, migrated devices, large emboli and the like. Thromboembolism occurs when part or all of a thrombus breaks away from the blood vessel wall. This clot (now called an embolus) is then carried in the direction of blood flow. An ischemic stroke may result if the clot lodges in the cerebral vasculature. A pulmonary embolism may result if the clot originates in the venous system or in the right side of the heart and lodges in a pulmonary artery or branch thereof. Clots may also develop and block vessels locally without being released in the form of an embolus—this mechanism is common in the formation of coronary blockages. There are significant challenges associated with designing clot removal devices that can deliver high levels of performance. First, there are a number of access challenges that make it difficult to deliver devices. In cases where access involves navigating the aortic arch (such as coronary or cerebral blockages) the configuration of the arch in some patients makes it difficult to position a guide catheter. These difficult arch configurations are classified as either type 2 or type 3 aortic arches with type 3 arches presenting the most difficulty.

The tortuosity challenge is even more severe in the arteries approaching the brain. For example it is not unusual at the distal end of the internal carotid artery that the device will have to navigate a vessel segment with a 180° bend, a 90° bend and a 360° bend in quick succession over a few centimetres of vessel. In the case of pulmonary embolisms, access is through the venous system and then through the right atrium and ventricle of the heart. The right ventricular outflow tract and pulmonary arteries are delicate vessels that can easily be damaged by inflexible or high profile devices. For these reasons it is desirable that the clot retrieval device be compatible with as low profile and flexible a guide catheter as possible.

Second, the vasculature in the area in which the clot may be lodged is often fragile and delicate. For example neurovascular vessels are more fragile than similarly sized vessels in other parts of the body and are in a soft tissue bed. Excessive tensile forces applied on these vessels could result in perforations and hemorrhage. Pulmonary vessels are larger than those of the cerebral vasculature, but are also delicate in nature, particularly those more distal vessels.

Third, the clot may comprise any of a range of morphologies and consistencies. Long strands of softer clot material may tend to lodge at bifurcations or trifurcations, resulting in multiple vessels being simultaneously occluded over significant lengths. More mature and organized clot material is likely to be less compressible than softer fresher clot, and under the action of blood pressure it may distend the compliant vessel in which it is lodged. Furthermore the inventors have discovered that the properties of the clot may be significantly changed by the action of the devices interacting with it. In particular, compression of a blood clot causes dehydration of the clot and results in a dramatic increase in both clot stiffness and coefficient of friction.

The challenges described above need to be overcome for any devices to provide a high level of success in removing clot and restoring flow. Existing devices do not adequately address these challenges, particularly those challenges associated with vessel trauma and clot properties.

SUMMARY

It is an object of the present design to provide devices and methods to meet the above-stated needs. It is therefore desirable for a clot retrieval device to remove clot from cerebral arteries in patients suffering AIS, from coronary native or graft vessels in patients suffering from MI, and from pulmonary arteries in patients suffering from PE and from other peripheral arterial and venous vessels in which clot is causing an occlusion.

In some examples, a clot retrieval device is disclosed to remove clot from a blood vessel. The device can include a collapsed configuration and an expanded configuration. The device can include an inner expandable body with a framework of struts. The device can include an outer expandable body with a framework of struts that form closed cells larger than the closed cells of the inner expandable body and at least partially radially surrounding the inner expandable body. The outer expandable body can include a distal scaffolding zone with a plurality of struts that distally taper with closed cells smaller than cells proximal thereof in the outer expandable body. The plurality of closed cells of the distal scaffolding zone can include a first plurality of closed cells being axially aligned smaller diamond shaped cells formed by struts of the distal scaffolding zone; a second plurality of closed cells being larger than cells of the first plurality of closed cells and radially separated, each smaller diamond shaped cell being radially inward and distal of each of the second plurality of closed cells; and a third plurality of closed cells radially separated and proximal of each of the second plurality of closed cells.

In some examples, the first plurality of closed cells can include a different shape than the second plurality of cells. The second plurality of closed cells can include a different shape than the third plurality of closed cells.

In some examples, the distal scaffolding zone can be a protective strut structure can include at least twelve closed cells between the first, second, and third plurality of closed cells.

In some examples, the first plurality of closed cells can include a pair of axially aligned smaller diamond shaped cells formed by struts of the distal portion and positioned along upper and lower regions of the distal scaffolding zone.

In some examples, each diamond shaped cell can include a best fit diameter of approximately 1.2 mm.

In some examples, the second plurality of closed cells can include at least four cells.

In some examples, the at least four cells can include a best fit diameter of approximately 1.6 mm.

In some examples, each of the at least four cells can share only one common edge with one of the smaller diamond shaped cells.

In some examples, each of the at least four cells can be a pentagon.

In some examples, the third plurality of radially separated cells can include at least five radially separated cells proximal of the second plurality of cells.

In some examples, struts of the distal scaffolding zone are connected to the inner expandable body.

In some examples, struts of the distal scaffolding zone form a mesh-like structure.

In some examples, the distal scaffolding zone can include a porosity greater than a porosity provided by the plurality of struts of the outer expandable body proximal thereof.

In some examples, a clot retrieval device is disclosed to remove clot from a blood vessel. The device can include a collapsed configuration and an expanded configuration. The device can include an inner expandable body with a framework of struts. The device can include an outer expandable body with a framework of struts that at least partially radially surrounding the inner expandable body. A distal portion of the outer expandable body can extend in the deployed configuration towards the outer expandable body to a greater extent than the inner expandable body, closed cells of the distal portion distally tapering and being smaller than cells proximal thereof in the outer expandable body. The plurality of closed cells of the distal portion can include a pair of axially aligned smaller diamond shaped cells formed by struts of the distal portion and positioned along upper and lower regions of the distal portion.

In some examples, the distal portion is a protective strut structure that can include at least twelve closed cells of the plurality of closed cells.

In some examples, the plurality of closed cells of the distal portion can include at least four radially separated larger cells, each smaller diamond shaped cell being radially inward and distal of the at least four radially separated larger cells.

In some examples, the at least four radially separated larger cells can include a best fit diameter of approximately 1.6 mm.

In some examples, each of the at least four radially separated larger cells sharing only one common edge with one of the smaller diamond shaped cells.

In some examples, each of the at least four radially separated larger cells form a pentagon.

In some examples, the plurality of closed cells of the distal portion can include at least five radially separated cells proximal of the at least four radially separated larger cells.

In some examples, the framework of struts of the outer expandable body can include a plurality of discontinuous expandable members spaced from adjacent expandable members, struts of each expandable can form closed cells with at least some struts terminating in radially separated distal apexes free from connection to an adjacent closed cell.

In some examples, the device can include a plurality of clot inlet mouths between respective expandable bodies through which clot may pass and enter the device.

In some examples, each member can include at least four radiopaque markers equally radially separated about a longitudinal axis of the outer expandable body.

In some examples, the at least four radiopaque markers being separated approximately 10 mm apart in the collapsed configuration.

In some examples, the at least four radiopaque markers being separated approximately 8 mm apart in the expanded configuration.

In some examples, the at least four radiopaque markers radiopaque markers can include radiopaque material positioned in an eyelet.

In some examples, the at least four radiopaque markers radiopaque markers can include at least one of Barium Sulphate, Bismuth SubCarbonate, Barium OxyChloride, Gold, Tungsten, Platinum, Iridium, Tantalum or an alloy of these materials.

In some examples, the device can include at least three expandable members longitudinally spaced apart.

In some examples, the plurality of closed cells of the distal portion forming a distal mesh; the inner expandable body can include a closed distal portion and the distal portion of the outer expandable body being closed; and the distal portion of the outer and inner expandable bodies together configured to prevent distal egress of clot or clot fragments from the device.

In some examples, the outer expandable body being expandable to a radial extent greater than the inner expandable body to define a clot reception space eccentrically arranged about a longitudinal axis of the outer tubular body.

In some examples, the outer expandable body can include a closed distal portion.

In some examples, a plurality of distal struts of the closed distal portion are spiraled.

In some examples, a plurality of distal struts of the closed distal portion extend normal to a longitudinal axis of the outer expandable body.

In some examples, a plurality of distal struts of the closed distal portion are configured in a bulged or flared pattern.

In some examples, the outer and inner expandable bodies each being monolithic structures.

In some examples, the outer expandable body can include at least two longitudinally spaced-apart expandable members connected by one or more struts configured as a longitudinal hinge between the spaced-apart expandable members, each expandable member can include a plurality of radially separated radiopaque markers.

In some examples, each marker is positioned at a junction between at least two connecting struts of a respective expandable member.

In some examples, each member can include at least four radiopaque markers equally radially separated about a longitudinal axis of the outer expandable body.

In some examples, the device can include at least three expandable members longitudinally spaced apart.

In some examples, the radiopaque markers can include radiopaque material positioned in an eyelet.

In some examples, the radiopaque markers can include at least one of Barium Sulphate, Bismuth SubCarbonate, Barium OxyChloride, Gold, Tungsten, Platinum, Iridium, Tantalum or an alloy of these materials.

In some examples, a diameter of the flow channel in the expanded configuration being less than 50% of a diameter of the outer expandable body in the expanded configuration along a longitudinally-extending clot reception space between the inner and outer expandable bodies.

In some examples, the device can include a shaft extended proximally of a proximal end of inner and/or outer expandable bodies.

In some examples, the device can include struts of the distal portion being connected to the inner expandable body.

Other aspects and features of the present disclosure will become apparent to those of ordinary skill in the art, upon reviewing the following detailed description in conjunction with the accompanying figures.

BRIEF DESCRIPTION OF THE DRAWINGS

The above and further aspects of this disclosure are further discussed with the following description of the accompanying drawings, in which like numerals indicate like structural elements and features in various figures. The drawings are not necessarily to scale, emphasis instead being placed upon illustrating principles of the disclosure. The figures depict one or more implementations of the inventive devices, by way of example only, not by way of limitation. It is expected that those of skill in the art can conceive of and combining elements from multiple figures to better suit the needs of the user.

DETAILED DESCRIPTION

Figure 1:
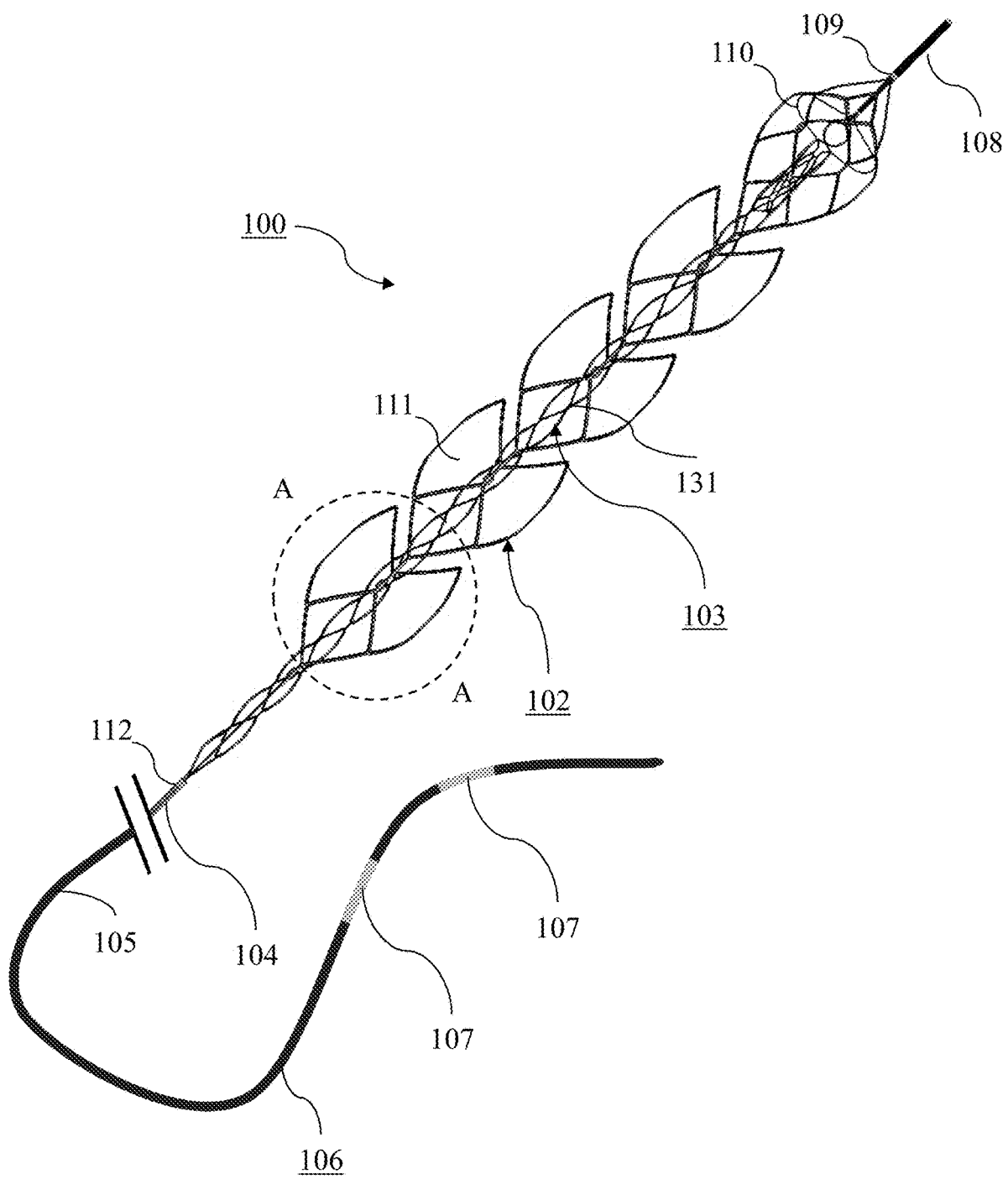
FIG. 1 shows an isometric view of a clot retrieval device of this disclosure.

Specific examples of the present disclosure are now described in detail with reference to the Figures, where identical reference numbers indicate elements which are functionally similar or identical. The examples address many of the deficiencies associated with traditional catheters, such as inefficient clot removal and inaccurate deployment of catheters to a target site.

Accessing the various vessels within the vascular, whether they are coronary, pulmonary, or cerebral, involves well-known procedural steps and the use of a number of conventional, commercially-available accessory products. These products, such as angiographic materials and guidewires are widely used in laboratory and medical procedures. When these products are employed in conjunction with the system and methods of this disclosure in the description below, their function and exact constitution are not described in detail.

The following detailed description is merely exemplary in nature and is not intended to limit the disclosure or the application and uses of the disclosure. Although the description of the disclosure is in many cases in the context of treatment of intracranial arteries, the disclosure may also be used in other body passageways as previously described.

It will be apparent from the foregoing description that, while particular embodiments of the present disclosure have been illustrated and described, various modifications can be made without departing from the spirit and scope of the disclosure. For example, while the embodiments described herein refer to particular features, the disclosure includes embodiments having different combinations of features. The disclosure also includes embodiments that do not include all of the specific features described. Specific embodiments of the present disclosure are now described in detail with reference to the figures, wherein identical reference numbers indicate identical or functionality similar elements. The terms "distal" or "proximal" are used in the following description with respect to a position or direction relative to the treating physician. "Distal" or "distally" are a position distant from or in a direction away from the physician. "Proximal" or "proximally" or "proximate" are a position near or in a direction toward the physician.

Accessing cerebral, coronary and pulmonary vessels involves the use of a number of commercially available products and conventional procedural steps. Access products such as guidewires, guide catheters, angiographic catheters and microcatheters are described elsewhere and are regularly used in cath lab procedures. It is assumed in the descriptions below that these products and methods are employed in conjunction with the device and methods of this disclosure and do not need to be described in detail. The following detailed description is merely exemplary in nature and is not intended to limit the disclosure or the application and uses of the disclosure. Although the description of the disclosure is in many cases in the context of treatment of intracranial arteries, the disclosure may also be used in other body passageways as previously described. A common theme across many of the disclosed designs is a dual layer construction in which the device includes an outer expandable member within which runs an inner expandable member, both members being directly or indirectly connected to an elongate shaft, and a distal net or scaffold configured at the distal end of the device to prevent the escape of clot fragments. This distal net may be appended to either the shaft, the inner or the outer members or to several of these. A range of designs are envisaged for each of these elements as described throughout this document, and it is intended that any of these elements could be used in conjunction with any other element, although to avoid repetition they are not shown in every possible combination.

For example both the inner and outer expandable members are desirably made from a material capable of recovering its shape automatically once released from a highly strained delivery configuration. A superelastic material such as Nitinol or an alloy of similar properties is particularly suitable. The material could be in many forms such as wire or strip or sheet or tube. A particularly suitable manufacturing process is to laser cut a Nitinol tube and then heat set and electropolish the resultant structure to create a framework of struts and connecting elements. This framework can be any of a huge range of shapes as disclosed herein and may be rendered visible under fluoroscopy through the addition of alloying elements (e.g., Platinum) or through a variety of other coatings or marker bands. The inner expandable member may in some cases form a generally tubular structure and is ideally configured to expand to a lesser diameter than that of the smallest vessel in which it is intended to be used. This diameter is typically less than 50% that of the outer expandable member may be as low as 20% or less of the outer member diameter. A range of different distal scaffolding zone designs are disclosed, some of which incorporate strut elements from the framework of the outer and/or inner expandable members, and some of which incorporate fine wires or fibers to provide added scaffolding with minimal impact of overall device profile or deliverability. Suitable materials ideally have a high tensile strength so that a very fine wire or fiber with sufficient integrity for manufacturability and use can be produced, such as for example polymers materials such as UHMWPE, Aramid, LCP, PET or PEN, or metals such as Tungsten, MP35N, stainless steel or Nitinol.

Figure 2:
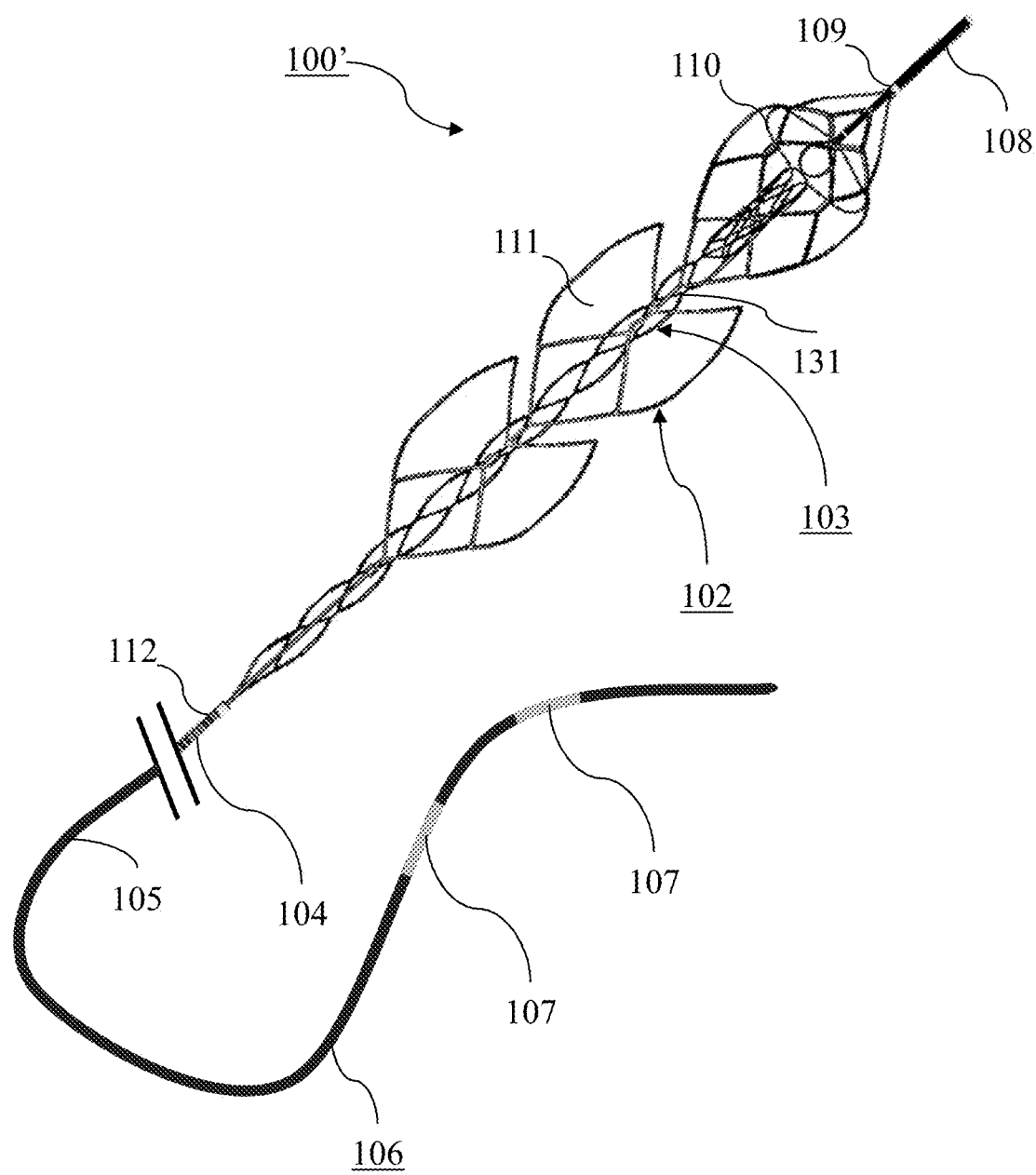
FIG. 2 shows an isometric view of another example of a clot retrieval device of this disclosure.
Figure 3:
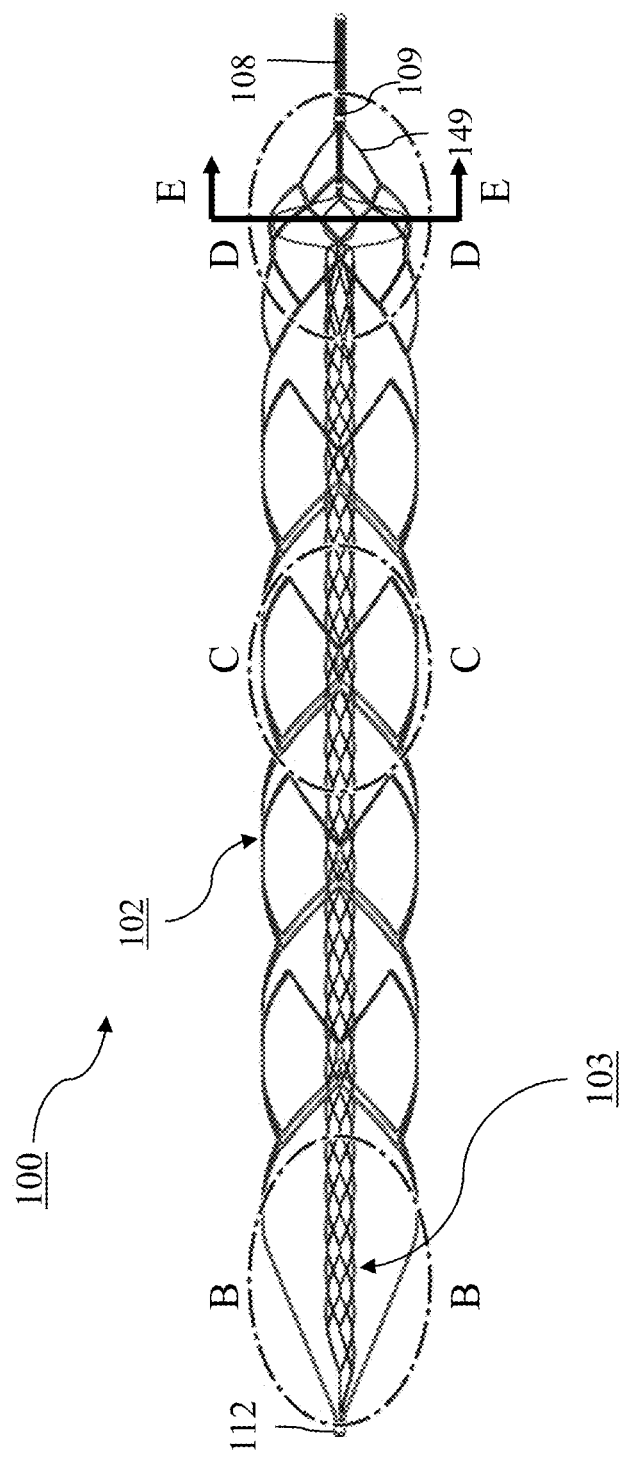
FIG. 3 shows a side view of the device of FIG. 1.

FIG. 1 shows one embodiment of a clot retrieval device 100 with an outer expandable member 102 and an inner expandable member 103 to facilitate restoration of blood flow through clot immediately after device 100 is deployed at an obstructive site. As shown, member 102 can include four (4) expandable members proximal of the distal portion. However, any number of expandable members are contemplated. For example, FIG. 2 shows a modified device 100' with fewer expandable member sections (e.g., two (2) as shown) of member 102. FIG. 3 shows a side of device 100 but without the proximal shaft. Device 100 has an elongate shaft 106 having a distal end that extends interior of the artery and a proximal end that extends exterior of the artery. Members 102 and 103 have a collapsed configuration for delivery and an expanded configuration for clot retrieval, flow restoration and fragmentation protection. Member 103 can have a generally tubular body section.

Member 103 is configured to self-expand upon release from a restraining sheath (e.g., a microcatheter) to a diameter larger than that of member 102. Expansion of member 102 can cause compression and/or displacement of the clot during expansion. When an expandable body provides a high level of scaffolding, the clot is compressed. When an expandable body provides an escape path or opening the expanding body will urge the clot towards the opening. However if the expandable body provides only modest scaffolding the clot will be displaced but since the clot has many degrees of freedom it may move in a variety of different directions and therefore cannot be controlled. By providing a tubular expandable body where the length of the tubular expandable body is substantially as long as the length of the occlusive clot or longer, many of the degrees of movement freedom available to the clot are removed.

Members 102 and 103 can specifically have a collapsed configuration for delivery and an expanded configuration for flow restoration and fragmentation protection. Members 102, 103 can be joined at the proximal and distal ends during assembly to minimize tension within members 102, 103 during use. In other examples, member 103 may not be connected to the distal end of member 102 at all or may be constrained within member 102 without being fixedly attached. In other examples, member 103 can have a non-cylindrical cross-section, may be non-uniform in diameter, and may have tailored strut patterns to provide regions of differing radial force or flexibility. The length of member 102 can be substantially the same as the length of member 103 in the freely expanded configuration and the loaded, collapsed configuration.

Member 103 can have an elastic or super-elastic or shape-memory metallic structure and can have a polished surface such as an electro-polished surface. Member 103 can be configured so as to provide a flow lumen or flow channel (e.g., generally cylindrical section) through device 100 to facilitate restoration of blood flow past the clot upon deployment. In one embodiment, member 103 is configured to scaffold the flow channel through the clot to prevent the liberation of fragments which might otherwise lodge in the distal vasculature. Member 103 can include one or more connected struts 131 configured to contact a clot when initially deployed in a target vessel within the clot. The contact of the one or more struts 131 with the clot provides additional grip and assists in the initial dislodgement of the clot from the vessel when device 100 is retracted.

The distal end of member 103 can include an expansile section formed from expanded struts 110 which have a diameter greater than that of member 103. These expanded struts 110 can be connected to a coil section 118 (see, e.g., FIG. 8) that can be laser cut from the tubing that member 103 can also be cut from. Coil 118 can also be configured to accommodate minor length differentials by stretching without applying significant tensile or compressive forces to device 100. Coil 118 can be formed from a stainless-steel material, a polymer or from a more radiopaque metal such as gold or platinum or an alloy of such a material. Coil 118 can be replaced with a longitudinal length of an elastic material such as a low modulus polymer or elastomer. The distal end of the coil 118 can be joined to the distal collar 109 of member 102 (e.g., by adhesive, a solder, weld or braze process). In some examples, struts 110 can elongate during loading so that the lengths of the members 102, 103 can be equal when fully loaded in a microcatheter. Length differentials between members 102, 103 can still occur when device 100 is deployed in a small vessel or during the loading or deployment process.

Members 102 and 103 are preferably made of a super-elastic or pseudo-elastic material such as Nitinol or another such alloy with a high recoverable strain. Shaft 106 may be a tapered wire shaft, and may be made of stainless steel, MP35N, Nitinol or other material of a suitably high modulus and tensile strength. Shaft 106 may have indicator bands 107 to indicate when the distal end of device 100 is approaching the end of the microcatheter during insertion. Shaft 106 can have a coil 104 adjacent its distal end and proximal of members 102, 103. Coil 104 may be metallic and may be formed from stainless steel or from a more radiopaque material such as platinum or gold for example or an alloy of such a material. In other examples, coil 104 can be coated with a low friction material or have a polymeric jacket positioned on the outer surface of the coil 104. Adjacent to coil 104 a sleeve 105 may be positioned on shaft 106. Sleeve 105 may be polymeric and may be positioned over a tapered section of shaft 106. Sleeve 105 may be rendered radiopaque through the addition of a filler material such as tungsten or barium sulphate. However, other radiopaque materials are contemplated, including but not limited to Bismuth SubCarbonate, Barium OxyChloride, Gold, Platinum, Iridium, Tantalum or an alloy of any of these materials. The sleeve 105 and shaft 106 may be coated with a material to reduce friction and thrombogenicity. The coating may include a polymer, a low friction lubricant such as silicon, a hydrophilic or a hydrophobic coating. This coating may also be applied to the member 102 and member 103.

Figure 4A:
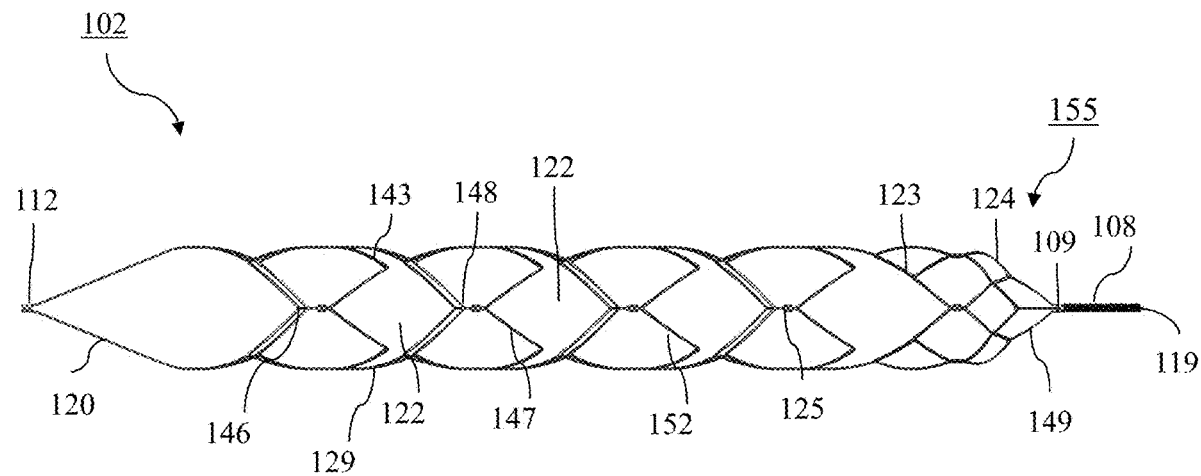
FIG. 4A shows a side plan view of the outer member of the clot retrieval device of FIGS. 1-2.
Figure 4B:
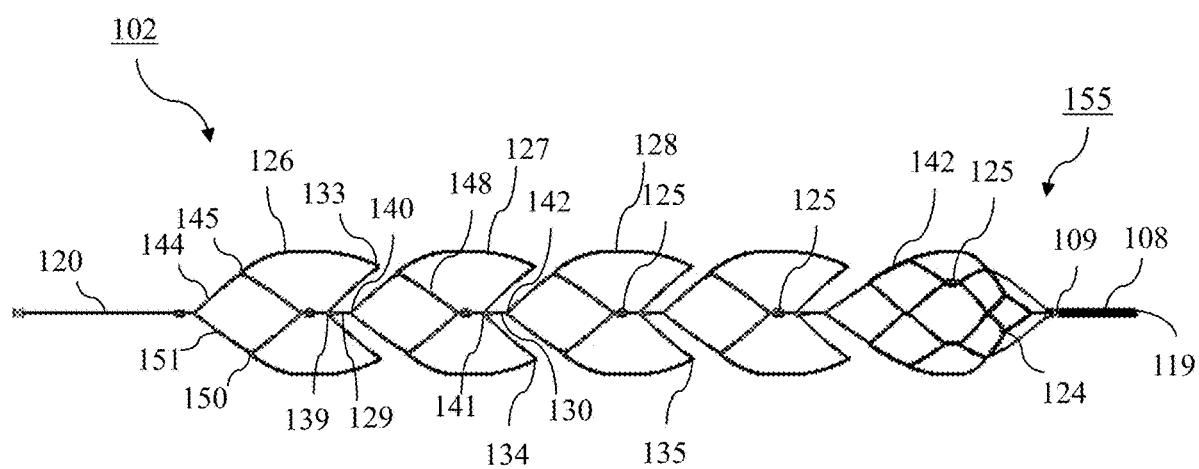
FIG. 4B shows a top plan view of the outer member of the clot retrieval device of FIGS. 1-2.

FIG. 4A shows a side plan view of member 102 while FIG. 4B shows a top plan view of member 102. Inlet openings 122 are provided in member 102 whereby inlets 122 can provide a primary movement freedom available to the clot and so the expansion of member 102 urges the clot into reception space 111. Member 102 can have multiple inlet mouths 122 to accept clot. Inlet mouths 122 can be configured to allow portions of the clot to enter reception space 111 and thus allow the clot to be retrieved without being excessively compressed. This is advantageous because the inventors have discovered that compression of clot causes it to dehydrate, which in turn increases the frictional properties of the clot, and increases its stiffness, all of which makes the clot more difficult to disengage and remove from the vessel. This compression can be avoided if the clot migrates inward through the wall of member 102 as the porous structure migrates outward towards the vessel wall.

The inlet mouths 122 can also provide the added benefit of allowing member 102 when retracted to apply a force to the clot in a direction substantially parallel to the direction in which the clot is to be pulled from the vessel (i.e. substantially parallel to the central axis of the vessel). This means that the outward radial force applied to the vasculature may be kept to a minimum, which in turn means that the action of the clot retrieval device 100 on the clot does not serve to increase the force required to dislodge the clot from the vessel, thus protecting delicate cerebral vessels from harmful radial and tensile forces.

Figure 6:
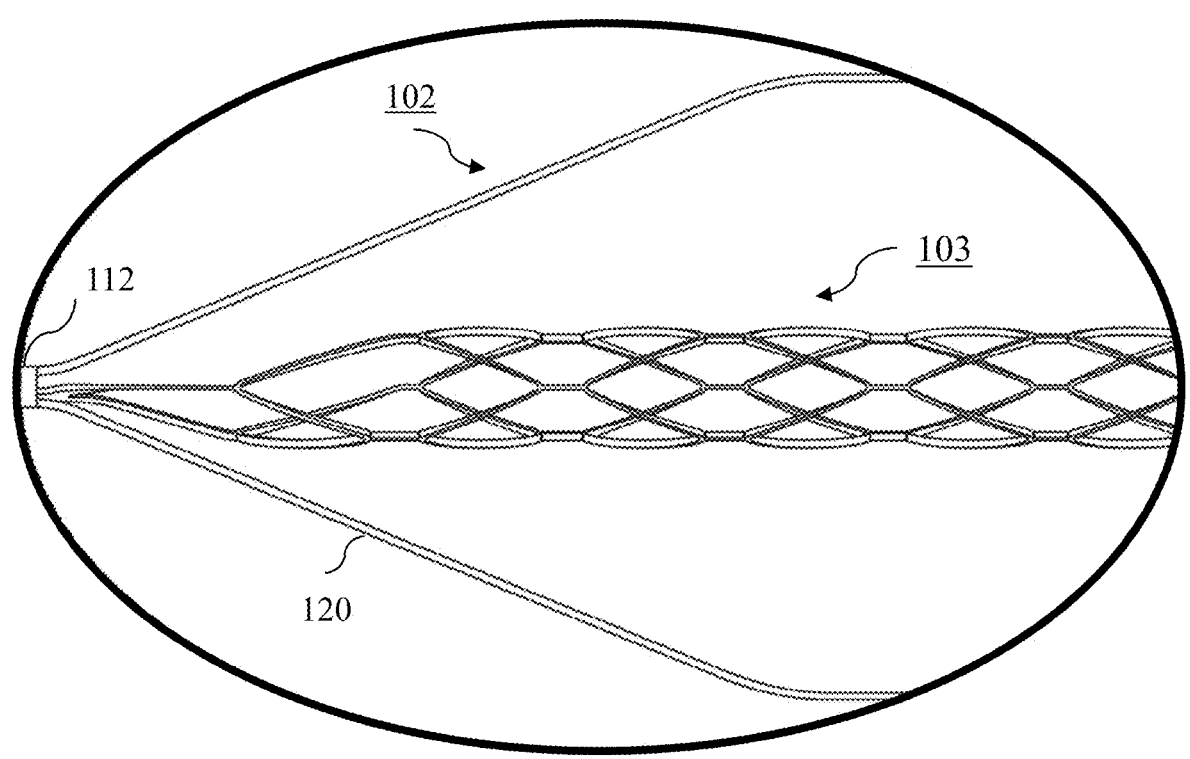
FIG. 6 shows a close-up view of section B-B of FIG. 3.

Member 102, as shown, can include proximal struts 120 connected at their proximal ends to collar 112 and at their distal ends to a first expandable member 126, which is more clearly shown in FIG. 6 at section B-B. As shown, struts 120 may have a tapered profile to ensure a gradual stiffness transition from shaft 106 to the clot engagement section of the device. Member 126 can be connected to a second expandable member 127 by a plurality of connecting arms 129, which can run from a proximal junction 139 to a distal junction 140. Arms 129 can include generally straight struts running parallel to the central axis of the device. In other embodiments these connecting arms may include a plurality of struts configured in one or more cells or may include curved or spiral arms. The region between the first and second expandable member includes two inlet mouths 122 through which clot may pass and enter the reception space 111 defined by the region between the inner and outer members.

Member 127 can in turn be connected to a third expandable member 128 by connecting arms 130, which run from a proximal junction 141 to a distal junction 142. Arms 130 can include generally straight struts running parallel to the central axis of device 100. In some examples, arms 130 can include a plurality of struts configured in one or more cells or may include curved or spiral arms. The region between members 127, 128 can include one or more inlet mouths 122 through which clot may pass and enter the reception space 111 defined by the region between members 102, 103. Arms 129 between members 126, 127 may be substantially aligned with arms 130 between members 127, 128 to align the neutral axis of members 126, 127, 128 during bending. In other examples, arms 129 between members 126, 127 may be aligned at an angle, such as 90 degrees, with arms 130 between members 127, 128.

Figure 7:
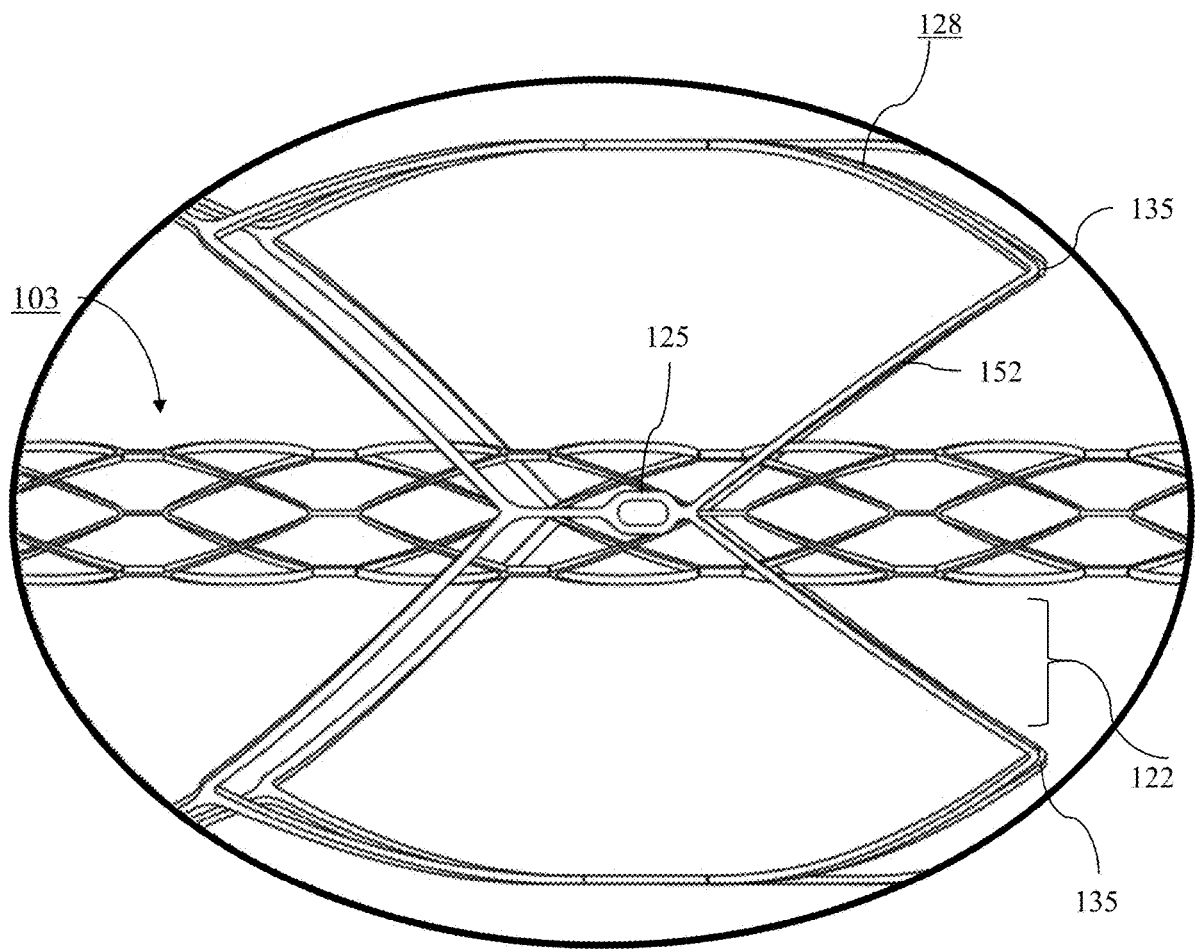
FIG. 7 shows a close-up view of section C-C of FIG. 3.

In some examples, member 126 can include interconnected struts, such as with strut 143 terminating in crowns 133 with no distal connecting elements, and other struts such as 144 terminating in junction points 145 and 146. Struts in the expandable members may be configured so that during loading, multiple crowns (e.g., crowns 145, 150) do not align at the same distance from the proximal collar 112. During loading or resheathing, a higher force can be generally required to load a crown than a strut into the sheath. Accordingly, if multiple crowns are loaded at the same time the user may notice an increase in loading force. By offsetting the crowns (e.g., crowns 145, 150) by making alternative struts 144 and 151 different lengths the loading force may be reduced and the perception to the user is improved. Similarly, second expandable member 127 can include interconnected struts, such as strut 147, terminating in crowns 134 with no distal connecting elements, and other struts (e.g., strut 148) terminating in junction points. Similarly, third expandable member 128 can include interconnected struts, such as strut 152, terminating in crowns 135 with no distal connecting elements, and other struts terminating in junction points. FIG. 7 shows a close-view of section C-C of FIG. 3 more clearly showing member 128 and its struts (e.g., strut 152) and crowns 135. As shown, fewer or great expandable members 126, 127, 128 may be included with member 102.

In some examples, expandable members of member 102 may include one or more markers 125 with radiopaque materials such as, but not limited to, a radiodense material such as Gold, Tungsten, Tantalum, Platinum or alloy containing these or other high atomic number elements. Polymer materials (e.g., polyurethane, pebax, nylon, polyethylene, or the like) might also be employed, containing a Radiopaque filler such as Barium Sulphate, Bismuth Sub-Carbonate, Barium OxyChloride, Gold, Tungsten, Platinum, Iridium, Tantalum, an alloy of these materials, and/or an adhesive filled with radiopaque filler. In this respect, marker 125 can be included as an eyelet on struts throughout member 102. Marker 125 can be positioned to indicate to the user the distal end of the barrel section of member 102 to aid in accuracy of deployment. The distal end of member 102 can include a circumferential ring of struts 123 connected to a series of struts 124 that can terminate at a distal junction point 109, which can include a collar. In some examples, member 102 can terminate in a closed distal end while in other aspects, the distal end of member 102 can be opened or not necessarily closed. In some examples, struts 124 may include a generally conical shape, as shown. In some examples, struts 124 can be arranged in a generally flat plane which may be inclined or may be normal to the longitudinal axis of device 100. Struts 124 and 149 can be tapered to a narrower width than those of the more proximal struts including the body of the expandable members (e.g., members 126, 127, 128, etc) thus creating a gradual transition in the stiffness of the device both in the expanded and collapsed states.

Figure 5:
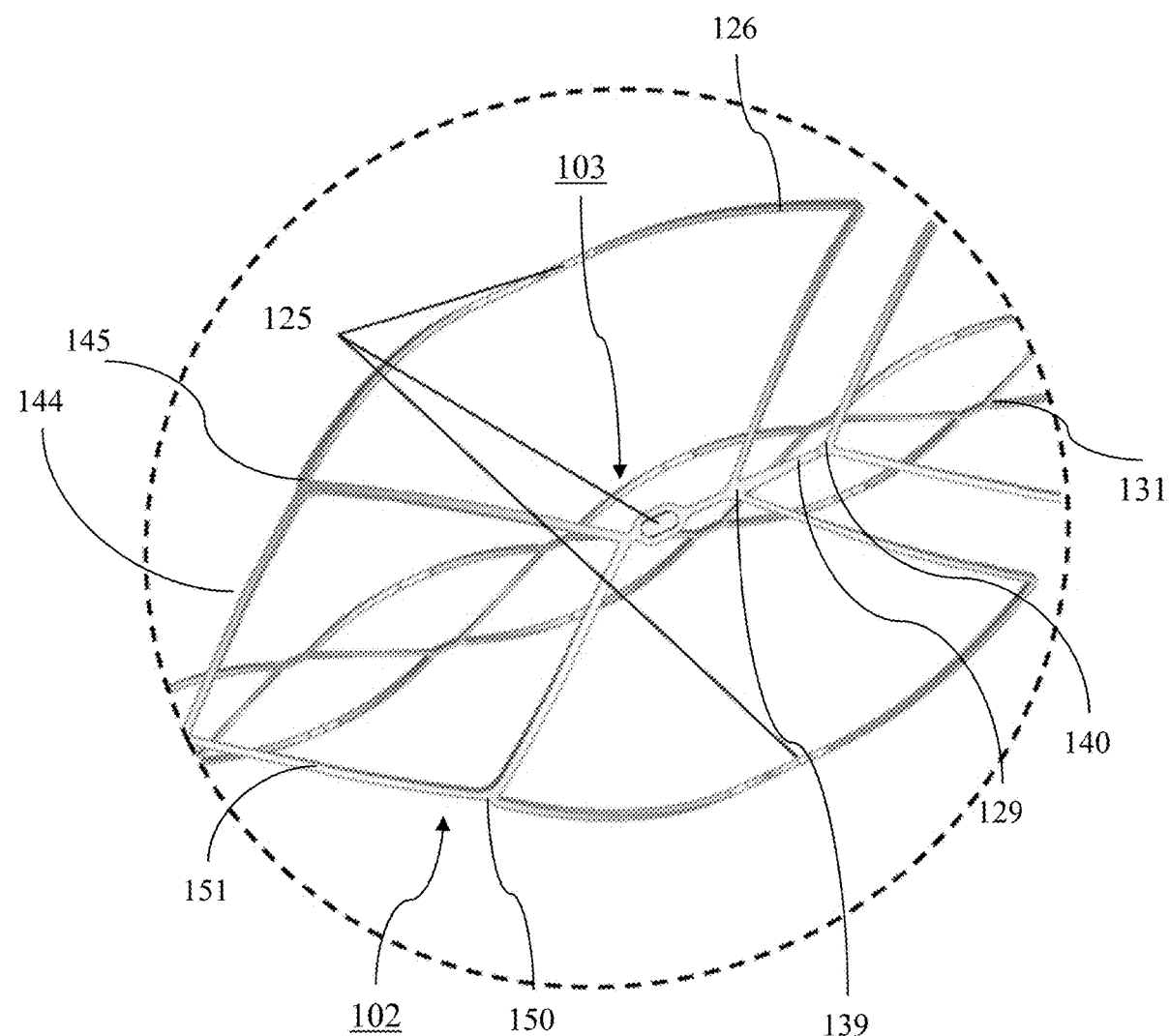
FIG. 5 shows a close-up view of section A-A of FIG. 1.

FIG. 5 is a close-up view of section A-A of FIG. 1 more clearly showing example markers 125 staggered on and along member 126. It is understood that the position of markers 125 as shown in FIG. 7 and throughout this disclosure are merely exemplary and markers 125 can be included elsewhere and with other features of device 100. In some examples, markers 125 can be separated approximately 10 mm apart in the collapsed, delivery configuration and be separated approximately 8 mm apart in the expanded configuration. However, markers 125 are not so limited and can separated as needed or required.

Figure 8:
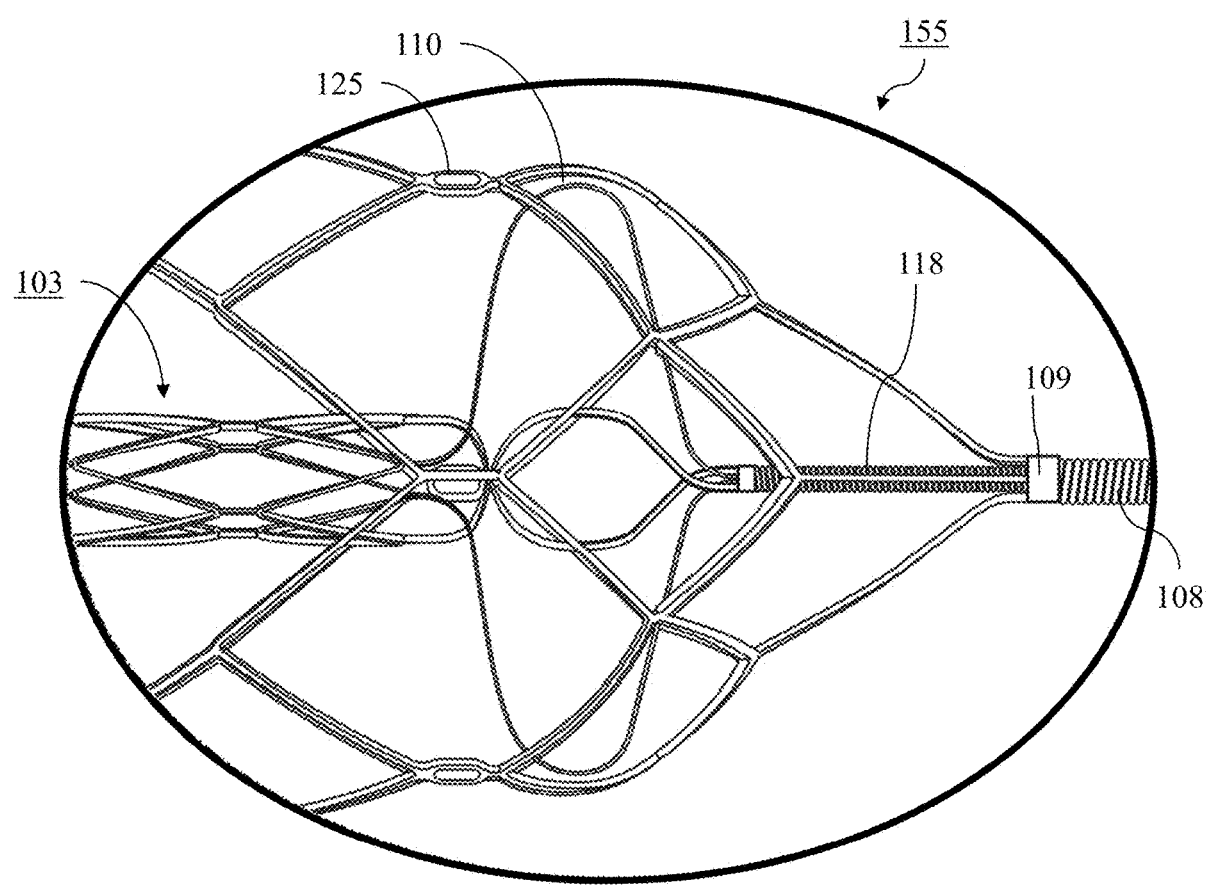
FIG. 8 shows a close-up view of section D-D of FIG. 3.
Figure 9:
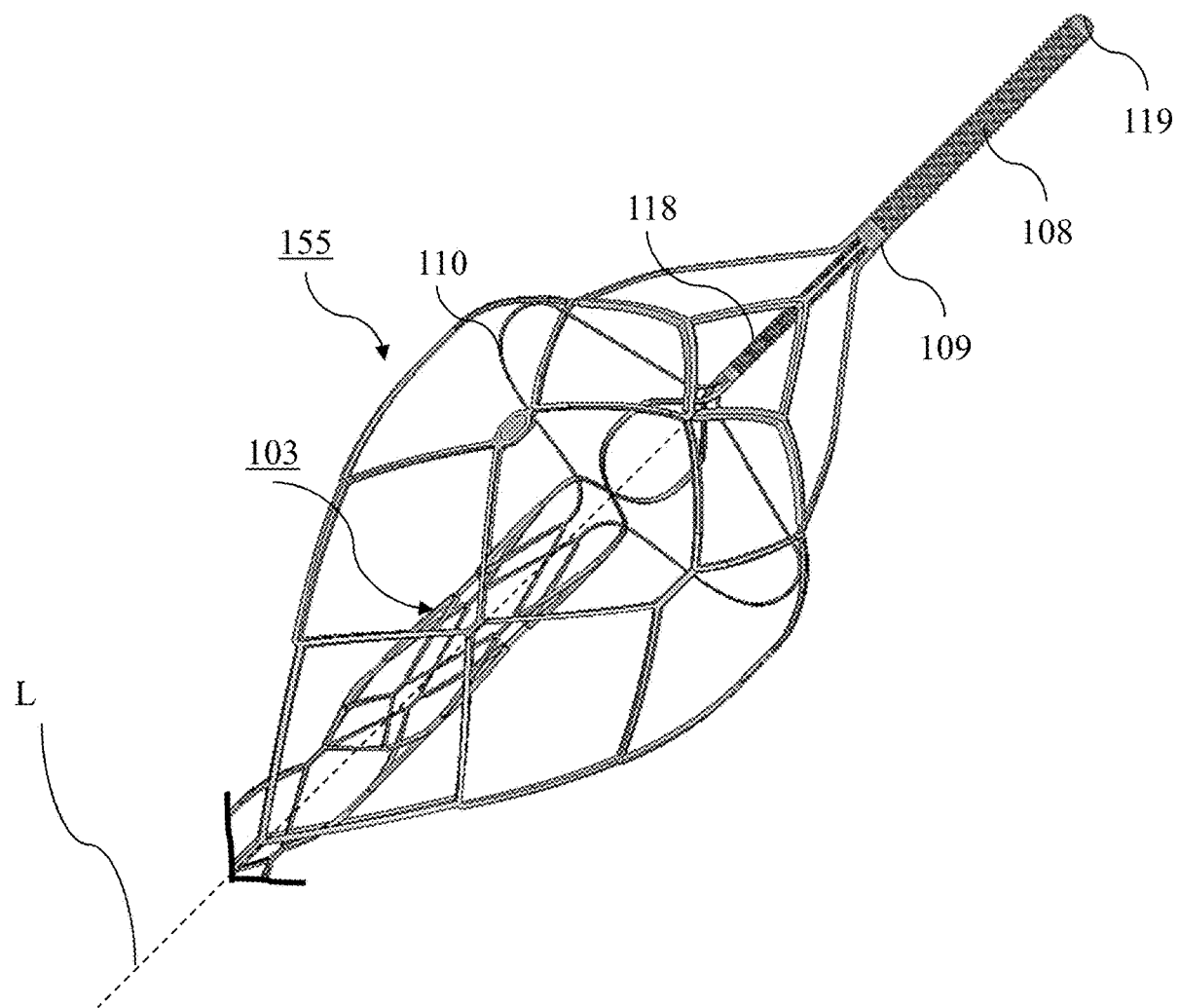
FIG. 9 shows a close-up isometric view of a distal region of the example clot retrieval device of FIG. 1.
Figure 10A:
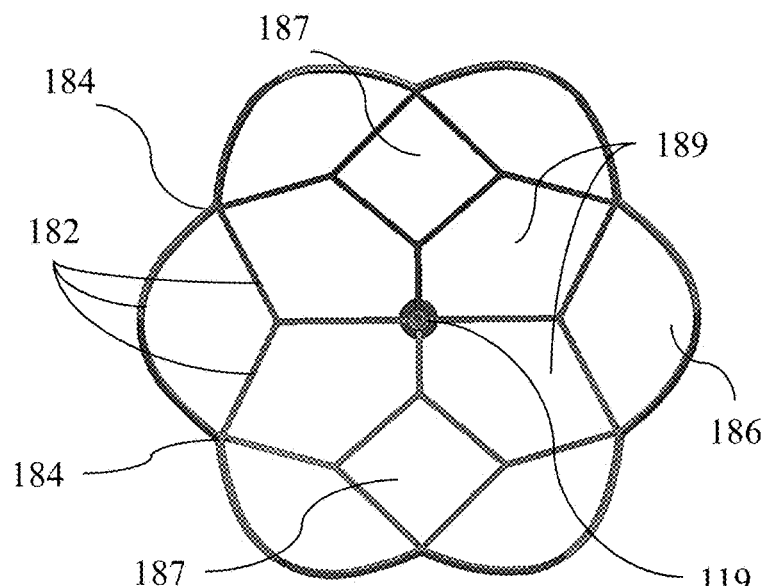
FIG. 10A shows an end view of the distal region of FIG. 9.
Figure 10C:
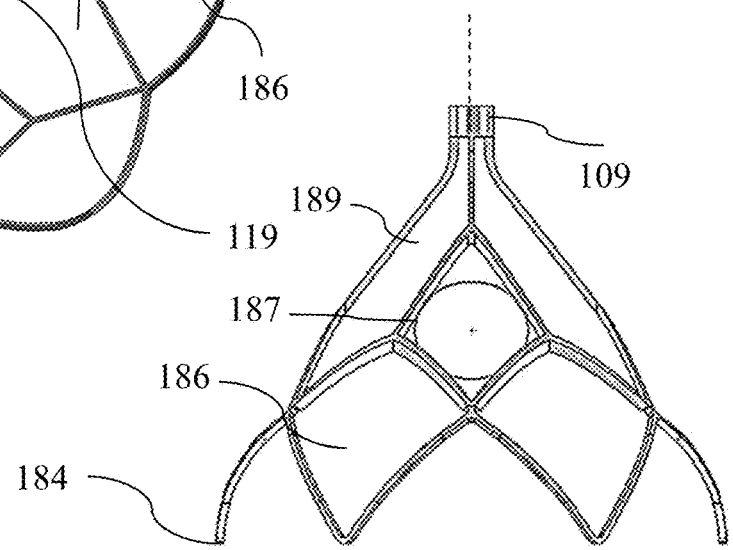
FIG. 10C shows a top view of the distal region of FIG. 9.
Figure 10B:
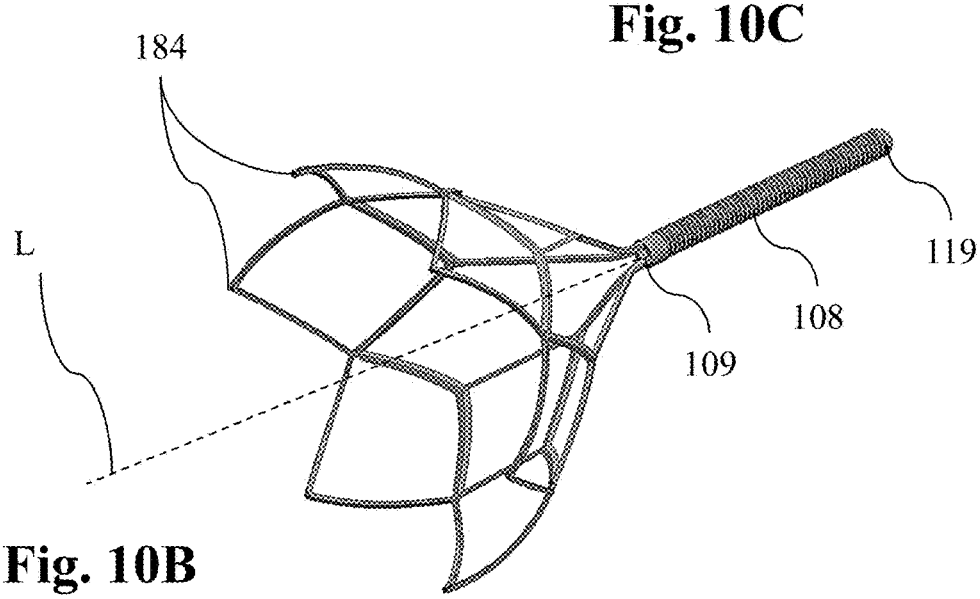
FIG. 10B shows an isometric view of the distal region of FIG. 9.

FIG. 8 shows a close-up view of section D-D of FIG. 3 more clearly showing distal region 155 while FIG. 9 shows close-up isometric view of a distal region 155 (sometimes referred herein interchangeably as a distal scaffolding zone) of device 100 at section E-E of FIG. 3. FIGS. 10A (end view) and 10B (isometric view) show the distal region 155 of member 102 only where a three-dimensional distal mesh of region 155 is configured for fragment protection feature is created by a framework of struts. As shown, a plurality of apexes or crowns 184 of distal region 155 shown in FIGS. 9-10C are provided connected to a plurality of arms 182 proximal thereof, which terminate at a junction proximate collar 109. Arms 182 can be shaped as needed or required, including generally bowed or conical as depicted. Preferably, arms 182 form a plurality of closed cells gradually going from larger closed cells at or adjacent the proximal end of region 155 to smaller closed cells at or adjacent the distal end. In some examples, at least twelve closed cells can be provided in distal region 155 of device 100. The distal region 155 shown can include a closed distal end of member 102 which, together with the mesh formed by arms 182 of region 155 and corresponding closed cells, can prevent egress of clot or clot fragments that have entered the previously described reception space 111 between members 102,103.

In some examples, axially aligned smaller diamond shaped cells 187 can be formed by arms 182 and positioned along upper and lower regions of the distal mesh. In some examples, at least two cells 187 are provided. Larger cells 189 can be positioned radially about longitudinal axis L of device 100 and radially inward of cells 187. In some examples, at least four cells 189 are provided joined at or adjacent a junction proximate collar 109. In some examples, cells 189 can measure approximately 1.2 mm, said measurement being the size of a best fit diameter of a circle placed in respective cell (e.g., cell 187 of shown drawn in the top view of FIG. 10C). In other examples, cells 189 can measure larger (e.g., approximately 1.6 mm).

Cells 186 can also be provided proximal of cells 187, 189. In some examples, at least five (5) cells 186 radially separated about axis L can be positioned proximal of cells 187, 189. Each of cells 186 can include struts common with cells 187, 189 as well as crowns 184. In some examples, the proximal struts of each of cells 186 can be bowed or otherwise curved. In some examples, the distal region 155 of FIGS. 9-10C shown can be a monolithic structure integrally formed with regions of member 102 proximal thereof (e.g., by being laser machined from the same tube as the rest of member 102). In some examples, radiopaque coil 108 (e.g., formed of platinum, gold, an alloy, etc.) can be positioned distal of the distal region 155 configured to couple at or against distal collar 109.

Figure 11A:
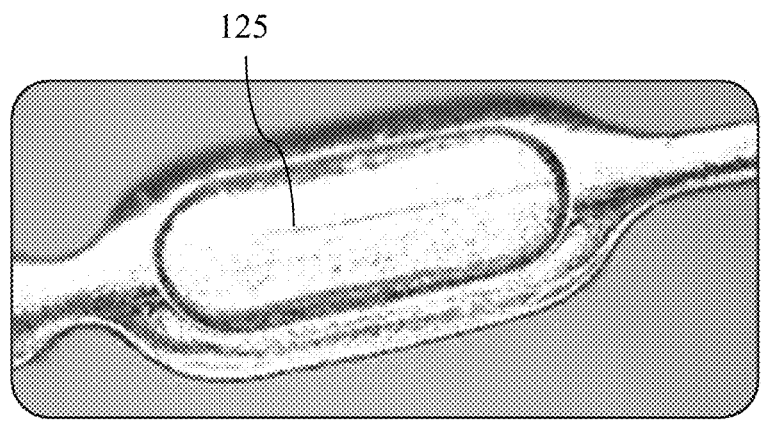
FIG. 11A shows a close-up isometric view of an example marker.
Figure 11B:
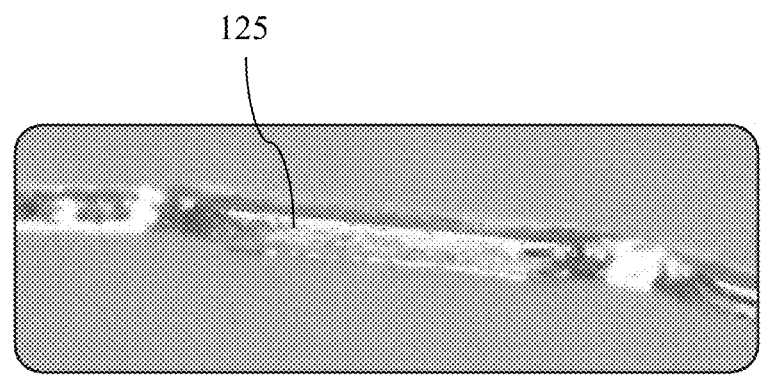
FIG. 11B shows a side plan view of the example marker of FIG. 11A.

FIG. 11A shows a close-up isometric view of an example marker 125 while FIG. 11B shows a side plan view of marker 125. The markers 125 shown are formed generally of platinum-iridium, though as previously discussed, other radiopaque materials are contemplated as needed or required.

Figure 12:
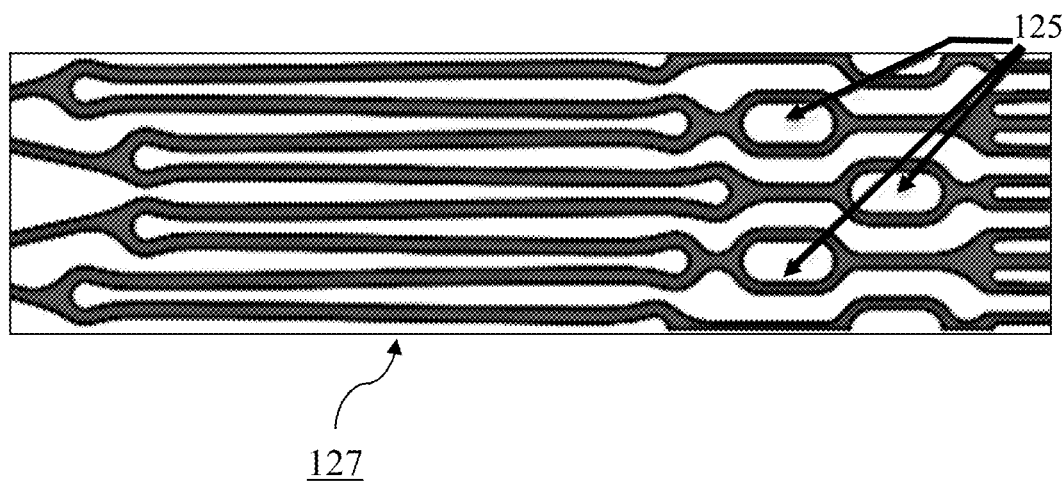
FIG. 12 shows a close-up of on expandable member of an example outer member in a collapsed configuration showing example laser cut patterns.

FIG. 12 shows a close-up of expandable member 127 in a collapsed configuration showing example laser cut patterns with enhanced visibility. It is understood that other expandable members of member 102 may follow the same or similar pattern. Member 12 may include three (3) eyelet cuts staggered for marker 125. In other examples, member 12 may include four (4) eyelet cuts staggered for marker 125. Fewer or greater eyelet cuts can be included as needed or required to incorporate markers 125. In those examples with 4 eyelet cuts, each expandable member of member 102 can include 4 markers 125. In this respect, if member 102 were to have three expandable members, then member 102 could include a total of at least twelve markers 125 staggered throughout. If member 102 were to have four expandable members, then at least twenty markers 125 could be included with member 102 staggered throughout.

The disclosure is not limited to the examples described, which can be varied in construction and detail. The terms "distal" and "proximal" are used throughout the preceding description and are meant to refer to a positions and directions relative to a treating physician. As such, "distal" or distally" refer to a position distant to or a direction away from the physician. Similarly, "proximal" or "proximally" refer to a position near to or a direction towards the physician.

In describing examples, terminology is resorted to for the sake of clarity. It is intended that each term contemplates its broadest meaning as understood by those skilled in the art and includes all technical equivalents that operate in a similar manner to accomplish a similar purpose. It is also to be understood that the mention of one or more steps of a method does not preclude the presence of additional method steps or intervening method steps between those steps expressly identified. Steps of a method can be performed in a different order than those described herein without departing from the scope of the disclosed technology. Similarly, it is also to be understood that the mention of one or more components in a device or system does not preclude the presence of additional components or intervening components between those components expressly identified.

As discussed herein, a "patient" or "subject" can be a human or any animal. It should be appreciated that an animal can be a variety of any applicable type, including, but not limited to, mammal, veterinarian animal, livestock animal or pet-type animal, etc. As an example, the animal can be a laboratory animal specifically selected to have certain characteristics similar to a human (e.g., rat, dog, pig, monkey, or the like).

As used herein, the terms "about" or "approximately" for any numerical values or ranges indicate a suitable dimensional tolerance that allows the part or collection of components to function for its intended purpose as described herein. More specifically, "about" or "approximately" may refer to the range of values±20% of the recited value, e.g. "about 90%" may refer to the range of values from 71% to 99%. Ranges can be expressed herein as from "about" or "approximately" one particular value and/or to "about" or "approximately" another particular value. When such a range is expressed, other exemplary embodiments include from the one particular value and/or to the other particular value.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It must also be noted that, as used in the specification and the appended claims, the singular forms "a," "an," and "the" include plural referents unless the context clearly dictates otherwise.

The descriptions contained herein are examples of the disclosure and are not intended in any way to limit the scope of the disclosure. While particular examples of the present disclosure are described, various modifications to devices and methods can be made without departing from the scope and spirit of the disclosure. For example, while the examples described herein refer to particular components, the disclosure includes other examples utilizing various combinations of components to achieve a described functionality, utilizing alternative materials to achieve a described functionality, combining components from the various examples, combining components from the various example with known components, etc. The disclosure contemplates substitutions of component parts illustrated herein with other well-known and commercially-available products. To those having ordinary skill in the art to which this disclosure relates, these modifications are often apparent and are intended to be within the scope of the claims which follow.

What is claimed is:

1. A clot retrieval device to remove a clot from a blood vessel, the device comprising a collapsed configuration and an expanded configuration and comprising:
   an inner expandable body comprising a framework of struts that form closed cells; and
   an outer expandable body comprising a framework of struts that form closed cells larger than the closed cells of the inner expandable body and at least partially radially surrounding the inner expandable body, the outer expandable body comprising a distal scaffolding zone comprising a plurality of struts that distally taper with closed cells smaller than cells proximal thereof in the outer expandable body;

the plurality of closed cells of the distal scaffolding zone comprising:
a radially aligned and joined group of a first plurality of closed cells being axially aligned small diamond shaped cells formed by struts of the distal scaffolding zone;
a radially aligned and joined group of a second plurality of closed cells being larger than cells of the first plurality of pentagon-shaped closed cells and radially separated, each small diamond shaped cell being radially inward, distal, and adjacent to the second plurality of closed cells; and
a third plurality of closed cells radially separated and proximal of each of the second plurality of closed cells;

wherein each of the second plurality of closed cells share common edges with two of the first plurality of closed cells; and wherein each of the first plurality of closed cells share common edges with two of the second plurality of closed cells.

2. The device of claim 1, the first plurality of closed cells comprising a different shape than the second plurality of cells; and
the second plurality of closed cells comprising a different shape than the third plurality of closed cells.

3. The device of claim 1, the distal scaffolding zone being a protective strut structure comprising at least twelve closed cells between the first, second, and third plurality of closed cells.

4. The device of claim 1, the first plurality of closed cells being a pair of axially aligned small diamond shaped cells formed by struts of the distal portion and positioned along upper and lower regions of the distal scaffolding zone.

5. The device of claim 4, each diamond shaped cell comprising a best fit diameter of approximately 1.2 mm.

6. The device of claim 4, the second plurality of closed cells comprising at least four cells.

7. The device of claim 6, the at least four cells comprising a best fit diameter of approximately 1.6 mm.

8. The device of claim 6, each of the at least four cells sharing only one common edge with one of the small diamond shaped cells.

9. The device of claim 6, the third plurality of closed cells comprising at least five radially separated cells proximal of the second plurality of cells.

10. A clot retrieval device to remove a clot from a blood vessel, the device comprising a collapsed configuration and an expanded configuration, and comprising:

an inner expandable body comprising a framework of struts; and
an outer expandable body comprising a framework of struts that at least partially radially surround the inner expandable body; and
a distal portion of the outer expandable body that extends in a radially outward direction in the expanded configuration, wherein small diamond shaped closed cells of the distal portion distally taper and are smaller than pentagon-shaped large closed cells adjacent proximal thereof;
the small diamond shaped closed cells of the distal portion comprising axially aligned cells formed by struts of the distal portion and positioned along upper and lower regions of the distal portion; and
wherein each of small diamond shaped closed cells share common edges with two of the large closed cells; and
wherein each of the large closed cells share common edges with two of the small diamond shaped closed cells.

11. The device of claim 10, wherein the distal portion being a protective strut structure comprises at least twelve closed cells.

12. The device of claim 10, wherein the large pentagon-shaped closed cells of the distal portion comprises at least four radially separated large cells, each small diamond shaped cell being radially inward and distal of the at least four radially separated large cells.

13. The device of claim 12, wherein the at least four radially separated large cells comprise a best fit diameter of approximately 1.6 mm.

14. The device of claim 12, wherein each of the at least four radially separated large cells share only one common edge with one of the small diamond shaped cells.

15. The device of claim 12, wherein the closed cells of the distal portion comprise at least five radially separated cells proximal of the at least four radially separated large cells.

16. The device of claim 10, wherein the framework of struts of the outer expandable body comprise a plurality of discontinuous expandable members spaced from adjacent expandable members, struts of each expandable forming closed cells with at least some struts terminating in radially separated distal apexes free from connection to an adjacent closed cell, each member comprising at least four radiopaque markers equally radially separated about a longitudinal axis of the outer expandable body.

17. The device of claim 16, wherein the at least four radiopaque markers are separated approximately 10 mm apart in the collapsed configuration.

18. The device of claim 16, wherein the at least four radiopaque markers radiopaque markers comprise at least one of Barium Sulphate, Bismuth SubCarbonate, Barium OxyChloride, Gold, Tungsten, Platinum, Iridium, Tantalum or an alloy of these materials.

* * * * *